(12) United States Patent
Boye et al.

(10) Patent No.: US 10,308,957 B2
(45) Date of Patent: Jun. 4, 2019

(54) RAAV VECTORS AND METHODS FOR TRANSDUCTION OF PHOTORECEPTORS AND RPE CELLS

(71) Applicant: University of Florida Research Foundation, Inc., Gainesville, FL (US)

(72) Inventors: Shannon E. Boye, Gainesville, FL (US); Sanford L. Boye, Gainesville, FL (US); Mavis Agbandje-McKenna, Gainesville, FL (US); Arun Srivastava, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/123,515

(22) PCT Filed: Mar. 4, 2015

(86) PCT No.: PCT/US2015/018791
§ 371 (c)(1),
(2) Date: Sep. 2, 2016

(87) PCT Pub. No.: WO2015/134643
PCT Pub. Date: Sep. 11, 2015

(65) Prior Publication Data
US 2016/0369299 A1 Dec. 22, 2016

Related U.S. Application Data

(60) Provisional application No. 61/947,940, filed on Mar. 4, 2014.

(51) Int. Cl.
| | |
|---|---|
| *C12N 15/86* | (2006.01) |
| *C07K 14/005* | (2006.01) |
| *A61K 48/00* | (2006.01) |
| *A61K 9/00* | (2006.01) |
| *A61K 9/51* | (2006.01) |

(52) U.S. Cl.
CPC ............ *C12N 15/86* (2013.01); *A61K 9/0048* (2013.01); *A61K 9/5184* (2013.01); *C07K 14/005* (2013.01); *A61K 48/00* (2013.01); *C12N 2750/14122* (2013.01); *C12N 2750/14143* (2013.01); *C12N 2810/6027* (2013.01)

(58) Field of Classification Search
None
See application file for complete search history.

(56) References Cited

U.S. PATENT DOCUMENTS

| | | | |
|---|---|---|---|
| 8,445,267 B2 | 5/2013 | Zhong et al. | |
| 8,802,080 B2 | 8/2014 | Warrington et al. | |
| 8,802,440 B2 | 8/2014 | Zhong et al. | |
| 9,157,098 B2 | 10/2015 | Zhong et al. | |
| 9,611,302 B2 | 4/2017 | Srivastava et al. | |
| 9,725,485 B2 | 8/2017 | Srivastava et al. | |
| 9,775,918 B2 | 10/2017 | Zhong et al. | |
| 2006/0088936 A1 | 4/2006 | Warrington et al. | |
| 2010/0203083 A1 | 8/2010 | Lux et al. | |
| 2013/0310443 A1 | 11/2013 | Srivastava et al. | |
| 2014/0050701 A1 | 2/2014 | Zhong et al. | |
| 2014/0341852 A1 | 11/2014 | Srivastava et al. | |
| 2015/0005369 A1 | 1/2015 | Muzyczka et al. | |
| 2016/0333372 A1 | 11/2016 | Srivastava et al. | |
| 2017/0275337 A1 | 9/2017 | Srivastava et al. | |
| 2018/0030096 A1 | 2/2018 | Aslanidi et al. | |
| 2018/0036428 A1 | 2/2018 | Zhong et al. | |
| 2018/0105559 A1 | 4/2018 | Srivastava et al. | |
| 2018/0223312 A1 | 8/2018 | Srivastava et al. | |
| 2018/0244727 A1 | 8/2018 | Zhong et al. | |

FOREIGN PATENT DOCUMENTS

| | | |
|---|---|---|
| EP | 1 486 567 A1 | 12/2004 |
| WO | WO 2007/089632 A2 | 8/2007 |
| WO | WO 2010/011404 A2 | 1/2010 |
| WO | WO 2010/093784 A2 | 8/2010 |
| WO | WO 2012/145601 A2 | 10/2012 |

(Continued)

OTHER PUBLICATIONS

O'Donnell et al. Adeno-Associated Virus-2 and Its Primary Cellular Receptor—Cryo-EM Structure of a Heparin Complex. Virology, 2009. 385:434-443.*
Lochrie et al. Mutations on the External Surfaces of Adeno-Associated Virus Type 2 Capsids That Affect Transduction and Neutralization. Journal of Virology, 2006. 80(2):821-834.*
Boye et al. Impact of Heparan Sulfate Binding on Transduction of Retina by Recombinant Adeno-Associated Virus Vectors. Journal of Virology, 2016. 90(8):4215-4231.*
International Preliminary Report on Patentability for Application No. PCT/US2015/018791 dated Sep. 15, 2016.
International Search Report and Written Opinion for Application No. PCT/US2015/018791 dated Aug. 12, 2015.
Supplementary European Search Report for Application No. EP 15758026.7 dated Nov. 3, 2017.

(Continued)

*Primary Examiner* — Christopher M Babic
*Assistant Examiner* — Kimberly A. Aron
(74) *Attorney, Agent, or Firm* — Wolf, Greenfield & Sacks, P.C.

(57) ABSTRACT

Disclosed are capsid-modified rAAV particles and expression vectors, as well as compositions and pharmaceutical formulations that comprise them. Also disclosed are methods of preparing and using novel capsid-protein-mutated particle or rAAV vector constructs in a variety of diagnostic and therapeutic applications including, inter alia, as delivery agents for diagnosis, treatment, or amelioration of one or more diseases, disorders, or dysfunctions of the mammalian eye. Also disclosed are methods for subretinal delivery of therapeutic gene constructs to mammalian photoreceptors and retinal pigment epithelial cells, as well as use of the disclosed compositions in the manufacture of medicaments for a variety of in vitro and/or in vivo applications including the treatment of a variety of inherited retinal diseases.

8 Claims, 3 Drawing Sheets
Specification includes a Sequence Listing.

(56) References Cited

FOREIGN PATENT DOCUMENTS

| | | | | |
|---|---|---|---|---|
| WO | WO-2012145601 A2 * | 10/2012 | ......... | A61K 48/0075 |
| WO | WO 2013/158879 A1 | 10/2013 | | |

OTHER PUBLICATIONS

Aslanidi et al., Abstract C240: Modification on the capsid of recombinant adeno-associated virus vectors (rAAV) leads to high-efficiency transduction of human monocyte-derived dendritic cells (moDCs). Mol Cancer Ther. Nov. 2011 10(11): Abstract C240. 3 Pages.

Aslanidi et al, High-Efficiency Transduction of Human Monocyte-Derived Dendritic Cells by Capsid-Modified Recombinant AAV2 Vectors. Vaccine. Jun. 6, 2012;30(26):3908-17. Author manuscript.

Aslanidi et al, Optimization of the Capsid of Recombinant Adeno-Associated Virus 2 (AAV2) Vectors: The Final Threshold?. PLoS One. 2013;8(3):e59142. doi: 10.1371/journal.pone.0059142. Epub Mar. 19, 2013 (12 pages).

Cheng et al, Development of Optimized AAV3 Serotype Vectors: Mechanism of High-Efficiency Transduction of Human Liver Cancer Cells. Gene Ther. Apr. 2012;19(4):375-84.

Doroudchi et al., Virally Delivered Channeirhodopsin-2 Safely and Effectively Restores Visual Function in Multiple Mouse Models of Blindness. Mol Ther. Jul. 2011;19(7):1220-9.

Gabriel et al., Targeted Mutagenesis of Ubiquitin-Binding Lysine Residues on the Adeno-Associated Virus (AAV)2 Capsid Improves Its Transduction Efficiency. Mol Ther. 2012;20(Supp 1):S146.

Jayandharan et al., Activation of the NF-κB Pathway by Adeno-Associated Virus (AAV) Vectors and its Implications in Immune Response and Gene Therapy. Proc Natl Acad Sci U S A. Mar. 1, 2011;108(9):3743-8. Retraction in: PNAS Jan. 9, 2018. 115 (2) E343; published ahead of print Dec. 26, 2017.

Kauss et al., Enhanced Long-Term Transduction and Multilineage Engraftment of Human Hematopoietic Stem Cells Transduced With Tyrosine-Modified Recombinant Adeno-Associated Virus Serotype 2. Hum Gene Ther. Sep. 2010;21(9):1129-36.

Kay et al., Targeting photoreceptors via intravitreal delivery using novel, capsid-mutated AAV vectors. PLoS One. Apr. 26, 2013;8(4):e62097. doi: 10.1371/journal.pone.0062097. Print 2013.

Ku et al., Gene Therapy Using Self-Complementary T733F Capsid Mutant AAV2/8 Restores Vision in a Model of Early Onset Leber Congenital Amaurosis. Hum Mol Genet. Dec. 1, 2011;20(23):4569-81.

Li et al., Site-Directed Mutagenesis of Surface-Exposed Lysine Residues Leads to Improved Transduction by Recombinant Aav2 and Aav8 Vectors in Murine Hepatocytes in Vivo. Mol Ther. 2013;21(Supp 1):S208-9.

Ling et al, Selective in vivo targeting of human liver tumors by optimized AAV3 vectors in a murine xenograft model. Hum Gene Ther. Dec. 2014;25(12):1023-34. doi: 10.1089/hum.2014.099.

Markusic et al., High-Efficiency Transduction and Correction of Murine Hemophelia B Using AAV2 Vectors Devoid of Multiple Surface-Exposed Tyrosines. Mol Ther. Dec. 2010;18(12):2048-56.

Nonnenmacher et al., Intracellular Transport of Recombinant Adeno-Associated Virus Vectors. Gene Therapy. Jun. 2012;19(6):649-658.

Opie et al., Identification of amino acid residues in the capsid proteins of adeno-associated virus type 2 that contribute to heparan sulfate proteoglycan binding. J Virol. Jun. 2003;77(12):6995-7006.

Pang et al., Long-Term Retinal Function and Structure Rescue Using Capsid Mutant AAV8 Vector in the rd10 Mouse, a Model or Recessive Retinitis Pigmentosa. Mol Ther. Feb. 2011;19(2):234-42. doi: 10.1038/mt.2010.273. Epub Dec. 7, 2010.

Petrs-Silva et al., High-Efficiency Transduction of the Mouse Retina by Tyrosine-Mutant AAV Serotype Vectors. Mol Ther. Mar. 2009;17(3):463-71.

Petrs-Silva et al., Novel Properties of Tyrosine-Mutant AAV2 Vectors in the Mouse Retina. Mol Ther. Feb. 2011;19(2):293-301.

Qiao et al., Adeno-Associated Virus Serotype 6 Capsid Tyrosine-to-Phenylalanine Mutations Improve Gene Transfer to Skeletal Muscle. Hum Gene Ther. Oct. 2010;21(10):1343-8.

Ruan et al., Development of an Anti-Angiogenic Therapeutic Model Combining scAAV2-delivered siRNAs and Noninvasive Photoacoustic Imaging of Tumor Vasculature Development. Cancer Lett. May 10, 2013;332(1):120-9. doi: 10.1016/j.canlet.2012.11.016. Epub Nov. 27, 2012.

Ryals et al., Quantifying Transduction Efficiencies of Unmodified and Tyrosine Capsid Mutant AAV Vectors in Vitro Using Two Ocular Cell Lines. Mol Vis. Apr. 29, 2011;17:1090-102.

Shin et al., A Simplified Immune Suppression Scheme Leads to Persistent Micro-Dystrophin Expression in Duchenne Muscular Dystrophy Dogs. Hum Gene Ther. Feb. 2012;23(2):202-9. doi: 10.1089/hum.2011.147. Epub Dec. 14, 2011.

Song et al., High-efficiency transduction of primary human hematopoietic stem cells and erythroid lineage-restricted expression by optimized AAV6 serotype vectors in vitro and in a murine xenograft model in vivo. PLoS One. 2013;8(3):e58757. doi: 10.1371/journal.pone.0058757. Epub Mar. 14, 2013.

Vandenberghe et al., Naturally occurring singleton residues in AAV capsid impact performance and illustrate structural constraints. Gene Ther. Dec. 2009;16(12):1416-28. doi: 10.1038/gt.2009.101.

Warrington et al., Adeno-associated virus type 2 VP2 capsid protein is nonessential and can tolerate large peptide insertions at its N terminus. Journal of Virology. Jun. 2004;78(12);6595-6609.

Zhong et al., A Dual Role of EGFR Protein Tyrosine Kinase Signaling in Ubiquitination of AAV2 Capsids and Viral Second-strand DNA Synthesis. Mol Ther. Jul. 2007;15(7):1323-30. Epub Apr. 17, 2007.

Zhong et al., Evaluation of Primitive Murine Hematopoietic Stem and Progenitor Cell Transduction In Vitro and In Vivo by Recombinant Adeno-Associated Virus Vector Serotypes 1 Through 5. Hum Gene Ther. Mar. 2006;17(3):321-33.

Zhong et al., Next generation of adeno-associated virus 2 vectors: Point mutations in tyrosines lead to high-efficiency transduction at lower doses. Proc Natl Acad Sci U S A. Jun. 3, 2008;105(22):7827-32. doi: 10.1073/pnas.0802866105. Epub May 29, 2008.

Aslanidi et al., Abstract 333: High-Efficiency Transduction of Primary Human Monocyte-Derived Dendritic Cells by Recombinant AAV6 Vectors Containing Mutations in Surface-Exposed Serine and Threonine Residues. Molecular Therapy. May 2013;21(S1):S129.

Aslanidi et al., Abstract 334: Optimization of the capsid of recombinant adeno-associated virus 2 (AAV2) vectors: the final threshold? Molecular Therapy. May 2013;21(S1):S129.

Wang et al., Limitations of encapsidation of recombinant self-complementary adeno-associated viral genomes in different serotype capsids and their quantitation. Hum Gene Ther Methods. Aug. 2012;23(4):225-33. doi: 10.1089/hgtb.2012.090.

* cited by examiner

US 10,308,957 B2

RAAV VECTORS AND METHODS FOR TRANSDUCTION OF PHOTORECEPTORS AND RPE CELLS

CROSS-REFERENCE TO RELATED APPLICATIONS

This application is a national stage filing under 35 U.S.C. § 371 of International PCT application PCT/US2015/018791, filed Mar. 4, 2015 which claims the benefit of the filing date of U.S. Provisional Application No. 61/947,940 filed Mar. 4, 2014, the entire contents of which are incorporated by reference herein.

STATEMENT REGARDING FEDERALLY SPONSORED RESEARCH OR DEVELOPMENT

This invention was made with government support under Grant Nos. P30EY021721, GM082946 and AI1081961 awarded by the National Institutes of Health. The government has certain rights in the invention.

FIELD OF THE INVENTION

The present invention relates generally to the fields of molecular biology and virology, and in particular, to the development of gene delivery vehicles.

BACKGROUND OF THE INVENTION

Major advances in the field of gene therapy have been achieved by using viruses to deliver therapeutic genetic material. The adeno-associated virus (AAV) has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, AAV DNA is packaged into the viral capsid as a single-stranded molecule about 4600 nucleotides (nt) in length. Following infection of the cell by the virus, the molecular machinery of the cell converts the single-stranded DNA into a double-stranded form. Only this double-stranded DNA form can be transcribed by cellular enzymes into RNA, which is then translated into polypeptides by additional cellular pathways.

Recombinant AAV (rAAV) has many properties that favor its use as a gene delivery vehicle: 1) the wild-type virus is not associated with any pathologic human condition; 2) the recombinant form does not contain native viral coding sequences; and 3) persistent transgenic expression has been observed in a variety of mammalian cells, facilitating their use in many gene therapy-based applications.

The transduction efficiency of AAV vectors varies greatly in different cells and tissues, in vitro and in vivo, and that fact limits their usefulness in certain gene therapy regimens. Systematic studies have been performed to elucidate the fundamental steps in the life cycle of AAV. For example, it has been documented that a cellular protein, FKBP52, phosphorylated at tyrosine residues by epidermal growth factor receptor protein tyrosine kinase (EGFR-PTK), inhibits AAV second-strand DNA synthesis and consequently, transgene expression in vitro as well as in vivo. It has also been demonstrated that EGFR-PTK signaling modulates the ubiquitin/proteasome pathway-mediated intracellular trafficking as well as FKBP52-mediated second-strand DNA synthesis of AAV vectors. In those studies, inhibition of EGFR-PTK signaling led to decreased ubiquitination of AAV capsid proteins, which in turn, facilitated nuclear transport by limiting proteasome-mediated degradation of AAV vectors, implicating EGFR-PTK-mediated phosphorylation of tyrosine residues on AAV capsids.

What is lacking in the prior art are improved, "next generation" rAAV viral vectors that demonstrate enhanced transduction efficiencies when infecting targeted mammalian cells, such as photoreceptors and retinal pigment epithelial cells of the human eye. The development of such vectors, as well as pharmaceutical formulations facilitating their administration to mammalian subjects would be a major advancement in the treatment of ocular diseases and disorders, and a significant step in realizing treatment of such conditions using viral-based gene therapies.

BRIEF SUMMARY OF THE INVENTION

The present disclosure overcomes these and other limitations inherent in the prior art by providing novel rAAV particles and vectors that are capable of, and optimized for, transducing one or more mammalian photoreceptors and/or mammalian retinal pigment epithelial cells following delivery of the viral particles, to a mammalian eye.

Advantageously, the novel rAAV particles, vectors, expression constructs, infectious virions, and pluralities of viral particles disclosed herein, in some embodiments, have improved efficiency in transducing one or more retinal cells of the mammalian eye, and in particular, improved efficiency in transducing one or more photoreceptor (PR) or retinal pigment epithelial (RPE) cells of the human eye.

The improved rAAV capsid-mutated particles and vectors contained therein described herein, in some embodiments, are able to transduce mammalian PR or RPE cells at higher-efficiencies (and often, much higher efficiencies) than the corresponding unmodified (i.e., "wild-type") rAAV vectors. By employing modified rAAV particles comprising modified capsid proteins that contain three, four, five, six, or seven or more surface-exposed amino acid residues substituted to non-native amino acids, the inventors have developed a collection of multi-mutated rAAV particles which may encapsidate vectors containing one or more cell-specific promoters each operably linked to a nucleic acid segment that encodes one or more diagnostic or therapeutic agents. The novel particles and vector constructs described herein have improved properties, and are capable of higher-efficiency transduction of PR and/or RPE cells than the corresponding, non-substituted (i.e., un-modified) parent vectors from which the mutant vectors were prepared.

The present disclosure provides AAV2-based particles and vectors for efficient delivery of transgenes to photoreceptors and/or retinal pigment epithelium (RPE) following subretinal injection. The disclosure also provides AAV2-based particles and vectors for efficient delivery of transgenes to photoreceptors and/or retinal pigment epithelium (RPE) following intravitreal injection. In an exemplary embodiment, the capsid modified "AAV2MAXΔHS" particle described herein transduces cells of outer retina (photoreceptors and RPE) much more efficiently than wild-type, unmodified AAV2. The levels of transgene expression achieved with this particle were on par with that achieved by two other AAV serotypes that are more commonly used to deliver transgene to these cells—AAV5 and AAV8.

The ability to transduce photoreceptors/RPE following intravitreal injection is a long sought after goal in the field. The AAV2-based particles and vectors with modulated HS affinity described herein accomplish such goals. Moreover, they drastically minimize the surgical risks associated with subretinal injection, significantly lower the cost of care, drastically increase the accessibility of gene therapies, and greatly simplify the current surgical process, by turning a major surgery into a routine outpatient procedure.

In some aspects, the disclosure provides a recombinant adeno-associated viral (rAAV) particle comprising a modified capsid protein, wherein the modified capsid protein comprises one or more non-native amino acid substitutions (e.g., one or more serines, threonines, or glycines, or a combination thereof) at positions corresponding to one or more heparan-sulfate-binding surface-exposed amino acid residues (e.g., one or more surface-exposed arginines) of a wild-type AAV2 capsid protein as set forth in SEQ ID NO:2; or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10. In some embodiments, the non-native amino acid substitutions occur at one or more (e.g., one, two or three) positions corresponding to one or more of: R585, R588, and R487 (e.g., R585, R588, R487, R585+R588, R585+R487, R588+R487, or R585+R588+R487) of a wild-type AAV2 capsid protein as set forth in SEQ ID NO:2, or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments of any one of the rAAV particles described herein, the modified capsid protein further comprises one or more non-native amino acid substitutions (e.g., phenylalanine or valine) at positions corresponding to one or more surface-exposed tyrosine and/or threonine residues of the wild-type AAV2 capsid protein as set forth in SEQ ID NO:2; or to tyrosine residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10. In some embodiments, the non-native amino acid substitutions occur at one or more (e.g., one, two, three, or four) positions corresponding to one or more of: Y444, T491, Y500, and Y730 of a wild-type AAV2 capsid protein as set forth in SEQ ID NO:2, or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments of any one of the rAAV particles described herein, the modified capsid protein further comprises a non-native substitution (e.g., a lysine) at a position that corresponds to E530 of a wild-type AAV2 capsid protein as set forth in SEQ ID NO:2, or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments of any of the modified capsid proteins described herein, the non-native amino acid substitutions occur at amino acid residues: (a) Y444, T491, Y500, R585, R588, R487, and Y730; (b) Y444, T491, Y500, R585, and Y730; (c) Y444, T491, Y500, R588, and Y730; (d) Y444, T491, Y500, R585, R588, and Y730; (e) Y444, T491, Y500, E530, R585, R588, R487, and Y730; (f) Y444, T491, Y500, E530, R585, and Y730; (g) Y444, T491, Y500, E530, R588, and Y730; or (h) Y444, T491, Y500, E530, R585, R588, and Y730 of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments, wherein the non-native amino acid substitutions comprise: (a) Y444F, T491V, Y500F, R585S, R588T, R487G, and Y730F; (b) Y444F, T491V, Y500F, R585S, and Y730F; (c) Y444F, T491V, Y500F, R588T, and Y730F; (d) Y444F, T491V, Y500F, R585S, R588T, and Y730F; (e) Y444F, T491V, Y500F, E530K, R585S, R588T, R487G, and Y730F; (f) Y444F, T491V, Y500F, E530K, R585S, and Y730F; (g) Y444F, T491V, Y500F, E530K, R588T, and Y730F; or (h) Y444F, T491V, Y500F, E530K, R585S, R588T, and Y730F of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments of any one of the rAAV particles described herein, the transduction efficiency of the particle is about 2- to about 50-fold higher in the one or more photoreceptor or RPE cells than that of a particle that comprises a corresponding, unmodified, wild-type capsid protein.

In some embodiments of any one of the rAAV particles described herein, the particle comprises a polynucleotide comprising a nucleic acid segment that encodes a diagnostic or therapeutic molecule operably linked to a promoter that is capable of expressing the nucleic acid segment in one or more photoreceptors or retinal pigment epithelial cells of a mammalian eye. In some embodiments, the nucleic acid segment further comprises an enhancer, a post-transcriptional regulatory sequence, a polyadenylation signal, or any combination thereof, operably linked to the nucleic acid segment encoding the therapeutic agent. In some embodiments, the nucleic acid segment expresses or encodes in one or more photoreceptor cells or RPE cells of a mammalian eye, a polypeptide, a peptide, a ribozyme, a peptide nucleic acid, an siRNA, an RNAi, an antisense oligonucleotide, an antisense polynucleotide, an antibody, an antigen binding fragment, or any combination thereof.

Other aspects of the disclosure relate to a method for transducing a mammalian photoreceptor cell or retinal pigment epithelium cell, the method comprising administering to one or both eyes of the mammal the rAAV particle of any one of the above embodiments, or as otherwise described herein. In some embodiments, the method comprises intravitreally or sub-retinally administering to one or both eyes of the mammal the rAAV particle.

Yet other aspects of the disclosure relate to a method for providing a mammal in need thereof with a therapeutically-effective amount of a selected therapeutic agent, the method comprising administering to one or both eyes of the mammal, an amount of the rAAV particle of any one of the above embodiments, or as otherwise described herein; and for a time effective to provide the mammal with a therapeutically-effective amount of the selected therapeutic agent. In some embodiments, the method comprises intravitreally or subretinally administering to one or both eyes of the mammal, an amount of the rAAV particle; and for a time effective to provide the mammal with a therapeutically-effective amount of the selected therapeutic agent.

Other aspects of the disclosure relate to a method for treating or ameliorating one or more symptoms of a disease, a disorder, a dysfunction, an injury, an abnormal condition, or trauma in a mammal, the method comprising, intravitreally or subretinally administering to one or both eyes of the mammal in need thereof, the rAAV particle of any one of the above embodiments, or as otherwise described herein, in an amount and for a time sufficient to treat or ameliorate the one or more symptoms of the disease, the disorder, the dysfunction, the injury, the abnormal condition, or the trauma in the mammal.

Other aspects of the disclosure relate to a method for expressing a nucleic acid segment in one or more photoreceptor cells or one or more RPE cells of a mammal, the method comprising: subretinally or intravitreally administering to one or both eyes of the mammal the rAAV particle of any one of the above embodiments, or as otherwise described herein, wherein the rAAV particle comprises a polynucleotide comprising at least a first polynucleotide that comprises a PR- or an RPE-cell-specific promoter operably linked to at least a first nucleic acid segment that encodes a therapeutic agent, for a time effective to produce the therapeutic agent in the one or more PR cells or RPE cells of the mammal.

In some embodiments, the mammal is human. In some embodiments, the human is a neonate, a newborn, an infant, or a juvenile. In some embodiments, the human has, is suspected of having, is at risk for developing, or has been diagnosed with a retinal disorder, a retinal disease, a retinal dystrophy, or any combination thereof. In some embodiments, the retinal disorder, retinal disease, or retinal dystrophy is inheritable.

In some embodiments, production of the therapeutic agent a) preserves one or more photoreceptor cells or one or more RPE cells, b) restores one or more rod- and/or cone-mediated functions, c) restores visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal. In some embodiments, production of the therapeutic agent persists in the one or more retinal cells substantially for a period of at least six months following an initial administration of the rAAV particle into the one or both eyes of the mammal.

In some embodiments, the therapeutic agent is an agonist, an antagonist, an anti-apoptosis factor, an inhibitor, a receptor, a cytokine, a cytotoxin, an erythropoietic agent, a glycoprotein, a growth factor, a growth factor receptor, a hormone, a hormone receptor, an interferon, an interleukin, an interleukin receptor, a nerve growth factor, a neuroactive peptide, a neuroactive peptide receptor, a protease, a protease inhibitor, a protein decarboxylase, a protein kinase, a protein kinsase inhibitor, an enzyme, a receptor binding protein, a transport protein or an inhibitor thereof, a serotonin receptor, or an uptake inhibitor thereof, a serpin, a serpin receptor, a tumor suppressor, a chemotherapeutic, or any combination thereof.

Other aspects of the disclosure relate to a nucleic acid vector that encodes a modified capsid protein, wherein the modified capsid protein comprises one or more non-native amino acid substitutions (e.g., one or more serines, threonines, or glycines, or a combination thereof) at positions corresponding to one or more heparan-sulfate-binding surface-exposed amino acid residues (e.g., one or more surface-exposed arginines) of a wild-type AAV2 capsid protein as set forth in SEQ ID NO:2; or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10. In some embodiments, the non-native amino acid substitutions occur at one or more (e.g. one, two or three) positions corresponding to one or more of: R585, R588, and R487 (e.g., R585, R588, R487, R585+R588, R585+R487, R588+R487, or R585+R588+R487) of a wild-type AAV2 capsid protein as set forth in SEQ ID NO:2, or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments, the modified capsid protein further comprises one or more non-native amino acid substitutions at positions corresponding to one or more surface-exposed tyrosine and/or threonine residues (e.g., phenylalanine or valine) of the wild-type AAV2 capsid protein as set forth in SEQ ID NO:2; or to tyrosine residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10. In some embodiments, the non-native amino acid substitutions occur at one or more (e.g., one, two, three, or four) positions corresponding to one or more of: Y444, T491, Y500, and Y730 of a wild-type AAV2 capsid protein as set forth in SEQ ID NO:2, or to amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments, the non-native amino acid substitutions occur at amino acid residues (a) Y444, T491, Y500, R585, R588, R487, and Y730; (b) Y444, T491, Y500, R585, and Y730; (c) Y444, T491, Y500, R588, and Y730; (d) Y444, T491, Y500, R585, R588, and Y730; (e) Y444, T491, Y500, E530, R585, R588, R487, and Y730; (f) Y444, T491, Y500, E530, R585, and Y730; (g) Y444, T491, Y500, E530, R588, and Y730; or (h) Y444, T491, Y500, E530, R585, R588, and Y730 of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

In some embodiments, the non-native amino acid substitutions comprise (a) Y444F, T491V, Y500F, R585S, R588T, R487G, and Y730F; (b) Y444F, T491V, Y500F, R585S, and Y730F; (c) Y444F, T491V, Y500F, R588T, and Y730F; (d) Y444F, T491V, Y500F, R585S, R588T, and Y730F; (e) Y444F, T491V, Y500F, E530K, R585S, R588T, R487G, and Y730F; (f) Y444F, T491V, Y500F, E530K, R585S, and Y730F; (g) Y444F, T491V, Y500F, E530K, R588T, and Y730F; or (h) Y444F, T491V, Y500F, E530K, R585S, R588T, and Y730F of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10. In some embodiments, the transduction efficiency of a particle comprising the modified capsid protein is about 2- to about 50-fold higher in one or more photoreceptor or RPE cells than that of a particle that comprises a corresponding, unmodified, wild-type capsid protein.

In some embodiments, the disclosure provides a recombinant adeno-associated viral (rAAV) vector that includes: a polynucleotide that encodes a modified capsid protein, wherein the modified capsid protein comprises at least a first non-native amino acid at a position that corresponds to a surface-exposed amino acid residue in the wild-type AAV2 capsid protein, and further wherein the transduction efficiency of a virion comprising the modified capsid protein is higher than that of a virion comprising a corresponding, unmodified wild-type capsid protein, and wherein the polynucleotide further comprises a nucleic acid segment that encodes a diagnostic or therapeutic molecule operably linked to a promoter that is capable of expressing the nucleic acid segment in one or more photoreceptors or retinal pigment epithelial cells of a mammalian eye, wherein the modified capsid protein comprises three or more non-native amino acid substitutions at positions corresponding to three distinct surface-exposed amino acid residues of the wild-type AAV2 capsid protein as set forth in SEQ ID NO:2; or to three distinct surface-exposed amino acid residues corresponding thereto in any one of the wild-type AAV1, AAV3, AAV4, AAV5, AAV6, AAV7, AAV9, or AAV10 capsid proteins, as set forth, respectively, in SEQ ID NO:3, SEQ ID NO:4, SEQ ID NO:5, SEQ ID NO:6, SEQ ID NO:7, SEQ ID NO:9, or SEQ ID NO:10, or any combination thereof.

Examples of the disclosed rAAV vector include, without limitation, those in which the non-native amino acid substitutions occur at amino acid residues: (a) Y444, Y500, and Y730; (b) Y272, Y444, Y500, and Y730; (c) Y444, T491, Y500, R585, R588, R487, and Y730; (d) Y444, T491, Y500, R585, and Y730; (e) Y444, T491, Y500, R588, and Y730; (f) Y444, T491, Y500, R585, R588, and Y730; (g) Y444, T491, Y500, and Y730; (h) Y444, T491, Y500, E530, R585, R588, R487, and Y730; (i) Y444, T491, Y500, E530, R585, and Y730; (j) Y444, T491, Y500, E530, R588, and Y730; (k) Y444, T491, Y500, E530, R585, R588, and Y730; or (l) Y444, T491, Y500, E530, and Y730; of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

In exemplary embodiments, the rAAV vectors of the disclosure include, but are not limited to those in which the non-native amino acid substitutions include: (a) Y444F, Y500F, and Y730F; (b) Y272F, Y444F, Y500F, and Y730F; (c) Y444F, T491V, Y500F, R585S, R588T, R487G, and Y730F; (d) Y444F, T491V, Y500F, R585S, and Y730F; (e) Y444F, T491V, Y500F, R588T, and Y730F; (f) Y444F, T491V, Y500F, R585S, R588T, and Y730F; (g) Y444F, T491V, Y500F, and Y730F; (h) Y444F, T491V, Y500F, E530K, R585S, R588T, R487G, and Y730F; (i) Y444F, T491V, Y500F, E530K, R585S, and Y730F; (j) Y444F, T491V, Y500F, E530K, R588T, and Y730F; (k) Y444F, T491V, Y500F, E530K, R585S, R588T, and Y730F; or (l) Y444F, T491V, Y500F, E530K, and Y730F; of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

In some embodiments, the vectors of disclosure have a transduction efficiency that is at least about 2- to about 50-fold higher in the one or more photoreceptor cells, or in one or more RPE cells, than that of a virion that comprises a corresponding, unmodified, wild-type capsid protein.

In some embodiments, the disclosed rAAV vectors will include a nucleic acid segment that further includes an enhancer, a post-transcriptional regulatory sequence, a polyadenylation signal, or any combination thereof, operably linked to the nucleic acid segment encoding the selected diagnostic or therapeutic molecule.

Exemplary molecules include, but are not limited to, polypeptides, peptides, ribozymes, peptide nucleic acids, siRNAs, RNAis, antisense oligonucleotides, antisense polynucleotides, antibodies (or antigen binding fragments thereof), as well as any combination thereof.

In other aspects of the disclosure, a method for providing a mammal in need thereof with a therapeutically-effective amount of a selected therapeutic agent is disclosed herein. Such a method generally includes at least the step of administering to one or both eyes of the mammal, an amount of one or more of the rAAV vectors disclosed herein; for a time effective to provide the mammal with a therapeutically-effective amount of the selected therapeutic agent.

The method may include, for example, the step or intravitreally or sub-retinally administering (single or repeated times) to either one or both eyes of the mammal, an amount of one or more rAAV vectors disclosed herein; and for a time effective to provide the mammal with a therapeutically-effective amount of the selected diagnostic or therapeutic agent.

In another embodiment, the disclosure provides a method for treating or ameliorating one or more symptoms of a disease, a disorder, a dysfunction, an injury, an abnormal condition, or trauma in a mammal. In an overall and general sense, such a method includes at least the step of administering to one or both eyes of the mammal in need thereof, one or more of the disclosed rAAV vectors herein, in an amount and for a time sufficient to treat or ameliorate the one or more symptoms of the disease, the disorder, the dysfunction, the injury, the abnormal condition, or the trauma in the mammal.

In another embodiment, the disclosure provides a method for expressing a nucleic acid segment in one or more photoreceptor cells or one or more RPE cells of a mammal (e.g., a human). In an overall and general sense, such a method includes administering (e.g., directly administering either subretinally or intravitreally) to one or both eyes of the mammal one or more of the rAAV vectors disclosed herein, wherein the polynucleotide further comprises at least a first polynucleotide that comprises a PR- or an RPE-cell-specific promoter operably linked to at least a first nucleic acid segment that encodes a therapeutic agent, for a time effective to produce the therapeutic agent in the one or more PR cells or RPE cells of the mammal. In some embodiments, the human is a neonate, a newborn, an infant, or a juvenile.

In the practice of the disclosure, it is contemplated that suitable patients will include, for example, humans that have, are suspected of having, are at risk for developing, or have been diagnosed with one or more retinal disorders, diseases, or dystrophies, including, without limitation, retinal disorders, diseases, and dystrophies that are genetically linked, or inheritable.

In some embodiments, the production of the therapeutic agent in the cells targeted for administration of the therapeutic construct will a) preserve one or more photoreceptor cells or one or more RPE cells, b) restore one or more rod- and/or cone-mediated functions, c) restore visual behavior in one or both eyes, or d) any combination thereof.

In some embodiments, production of the therapeutic agent persists in the one or more photoreceptor cells or the one or more RPE cells substantially for a period of at least three months, at least six months, at least nine months, or at least a year or more, following an initial administration of the rAAV gene therapy construct into the one or both eyes of the mammal. In some diseases, it may be preferable to administer the rAAV vector construct a single time, while in the management or treatment of other diseases or conditions, it may be desirable to provide two or more administrations of the vector constructs to the patient in one or more administration periods. In such circumstances, the AAV vector-based therapeutics may be provided successively in one or more daily, weekly, monthly, or less-frequent periods, as may be necessary to achieve treatment, or amelioration of one or more symptoms of the disease or disorder being treated. In some embodiment, the vector is a self-complementary rAAV (scAAV) vector, while in other embodiments, the vector may be provided to the one or both eyes by one or more administrations of an infectious adeno-associated viral particle, an rAAV virion, or a plurality of infectious rAAV particles in an amount and for a time sufficient to treat or ameliorate one or more symptoms of the disease or condition being treated.

In certain embodiments, the therapeutic agent may be an agonist, an antagonist, an anti-apoptosis factor, an inhibitor, a receptor, a cytokine, a cytotoxin, an erythropoietic agent, a glycoprotein, a growth factor, a growth factor receptor, a hormone, a hormone receptor, an interferon, an interleukin, an interleukin receptor, a nerve growth factor, a neuroactive peptide, a neuroactive peptide receptor, a protease, a protease inhibitor, a protein decarboxylase, a protein kinase, a protein kinsase inhibitor, an enzyme, a receptor binding protein, a transport protein or an inhibitor thereof, a serotonin receptor, or an uptake inhibitor thereof, a serpin, a serpin receptor, a tumor suppressor, a chemotherapeutic, or any combination thereof.

BRIEF DESCRIPTION OF THE DRAWINGS

For promoting an understanding of the principles of the disclosure, reference will now be made to the embodiments, or examples, illustrated in the drawings and specific language will be used to describe the same. It will, nevertheless be understood that no limitation of the scope of the disclosure is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which.

BRIEF DESCRIPTION OF THE SEQUENCES

Figures 1A, 1B, 1C, 1D:
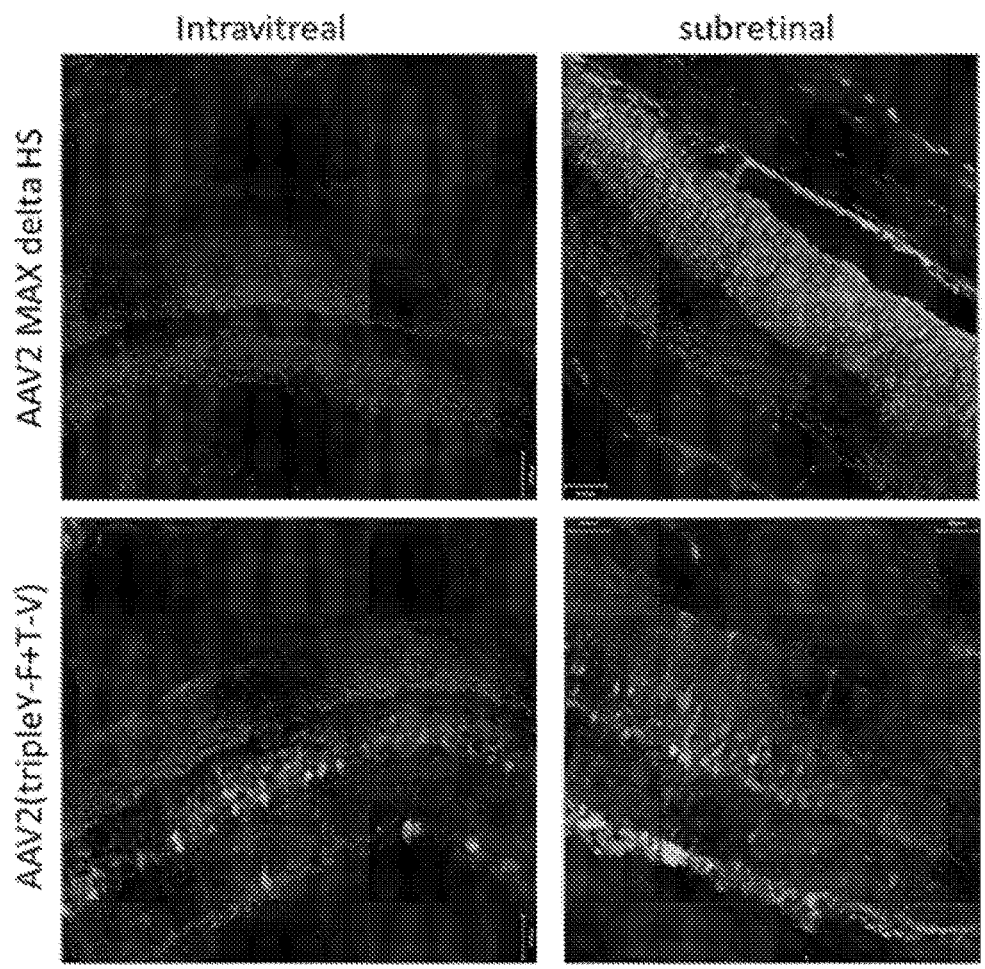
FIG. 1A, FIG. 1B, FIG. 1C, and FIG. 1D show the transduction profile of AAV2-based vectors containing ubiquitous CBA promoter and mCherry reporter following either intravitreal or subretinal injection in wild type mouse eyes. Vectors were delivered at a concentration of $1\times10^{12}$ vg/mL. AAV2MAXΔHS, which lacks canonical HS binding residues, fails to transduce retinal neurons following intravitreal injection (FIG. 1A) whereas its delivery to the subretinal space promotes robust transduction of both photoreceptors and RPE (FIG. 1B). This finding supports the notion that HS is not required for transduction of photoreceptors or RPE. Interestingly, the level of transduction seen with this vector is on par with that seen following subretinal injection of AAV5 or AAV8. AAV2(tripleY→F+T→V), which retains HS binding exhibits transduction of retinal neurons following delivery to either the subretinal space or vitreous (FIG. 1C and FIG. 1D)
Figure 2:
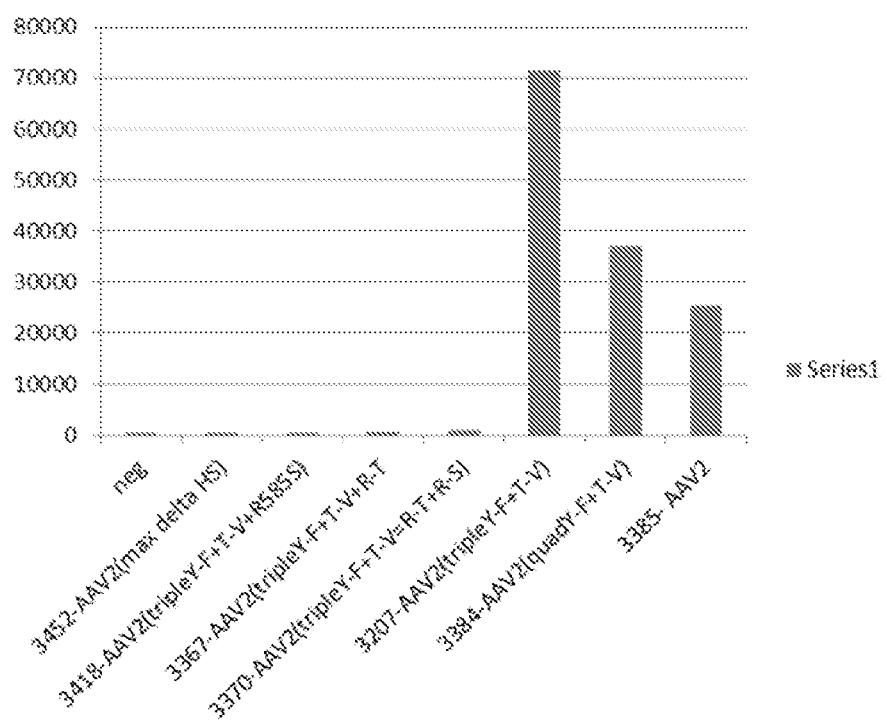
FIG. 2 shows the results of a study in which 661W cone photoreceptor cells were infected with AAV2-based vectors containing the ubiquitous CBA promoter and an mCherry reporter at an MOI of 5000. Three days later, mCherry fluorescence was quantified across samples with fluorescence-activated cell sorting (FACS). Because the ability to infect these cells depends on binding to HS, capsid mutants with reduced or ablated HS affinity demonstrate poor transduction.
Figure 3:
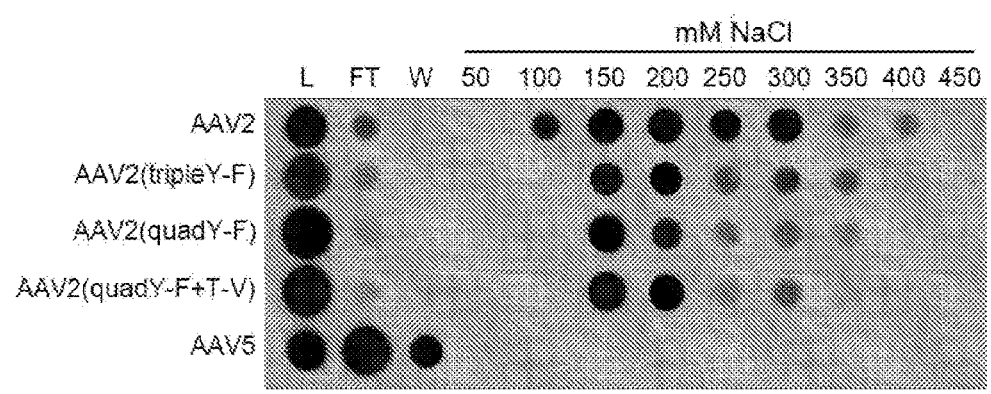
FIG. 3 illustrates the heparan sulfate (HS) binding of various AAV2-based capsid mutants constructed in accordance with certain aspects of the present invention.

SEQ ID NO:1 is an amino acid sequence of the capsid protein of the wild-type adeno-associated virus serotype 1 (AAV1);

SEQ ID NO:2 is an amino acid sequence of the capsid protein of the wild-type adeno-associated virus serotype 2 (AAV2);

SEQ ID NO:3 is an amino acid sequence of the capsid protein of the wild-type adeno-associated virus serotype 3 (AAV3);

SEQ ID NO:4 is an amino acid sequence of the capsid protein of the wild-type adeno-associated virus serotype 4 (AAV4);

SEQ ID NO:5 is an amino acid sequence of the capsid protein of the wild-type adeno-associated virus serotype 5 (AAV5);

SEQ ID NO:6 is an amino acid sequence of the capsid protein of the wild-type adeno-associated virus serotype 6 (AAV6);

SEQ ID NO:7 is an amino acid sequence of the capsid protein of the wild-type adeno-associated virus serotype 7 (AAV7);

SEQ ID NO:8 is an amino acid sequence of the capsid protein of the wild-type adeno-associated virus serotype 8 (AAV8);

SEQ ID NO:9 is an amino acid sequence of the capsid protein of the wild-type adeno-associated virus serotype 9 (AAV9); and SEQ ID NO:10 is an amino acid sequence of the capsid protein of the wild-type adeno-associated virus serotype 10 (AAV10).

It is to be understood that SEQ ID NOs: 1-10 refer to exemplary VP1 capsid proteins and that VP2 and VP3 capsid proteins are shorter variants of the VP1 capsid protein generally having a truncated N-terminus compared to VP1.

For example, VP2 of AAV2 may lack the first 137 amino acids of VP1 and VP3 of AAV2 may lack the first 202 amino acids of VP1.

DESCRIPTION OF ILLUSTRATIVE EMBODIMENTS

Illustrative embodiments of the disclosure are described below. The unique ability of the disclosed vectors to selectively- and exclusively-target PR or RPE cells facilitates multiple uses in vivo. First, it aids in the development of gene replacement strategies for inherited retinal diseases associated with mutations in PR- and/or RPE-specific genes including, for example, genes that are responsible for one or more inherited retinal diseases.

In a particular embodiment the disclosure provides improved rAAV vectors that have been derived from a number of different serotypes, including, for example, those selected from the group consisting of AAV1, AAV2, AAV3, AAV4, AAV5, AAV6, AAV7, AAV8, AAV9, and AAV10, whose exemplary capsid protein sequences are set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, herein, respectively.

Exemplary multi-mutated VP3 capsid protein modified rAAV particles of the present disclosure include, but are not limited to, those comprising three, four, five, six, or seven or more non-native amino acid substitutions at three, four, five, six, or seven or more amino acid residues selected from the group consisting of: (a) Tyr444, Arg487, Thr491, Tyr500, Glu530, Arg585, Arg588, and Tyr730 of the wild-type AAV2 capsid protein as set forth in SEQ ID NO:2; and (b) three, four, five, six, or seven or more non-native amino acid substitutions at three, four, five, six, or seven or more equivalent amino acid positions corresponding thereto, in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

The disclosure also provides an isolated and purified polynucleotide that encodes one or more of the disclosed rAAV vectors or capsid proteins described herein, as well as pluralities of infectious adeno-associated viral virions that contain such a polynucleotide. In some embodiments, the vector constructs of the present disclosure include or further include at least one nucleic acid segment that encodes at least one ocular therapeutic agent operably linked to a photoreceptor- or RPE-specific promoter that is capable of expressing the nucleic acid segment in suitable mammalian retinal cells that have been transformed with the vector construct.

In some embodiments, the transduction efficiency of a particle comprising a multi-mutated, capsid protein will be higher than that of the corresponding, unmodified, wild-type protein, and as such, will possess a transduction efficiency in mammalian retinal cells that is at least 2-fold, at least about 4-fold, at least about 6-fold, at least about 8-fold, at least about 10-fold, or at least about 12-fold or higher in a selected mammalian host cell than that of a virion that comprises a corresponding, unmodified, capsid protein. In certain embodiments, the transduction efficiency of the rAAV particles provided herein will be at least about 15-fold higher, at least about 20-fold higher, at least about 25-fold higher, at least about 30-fold higher, or at least about 40, 45, or 50-fold or more greater than that of a virion that comprises a corresponding, unmodified, capsid protein. In some embodiments, the infectious virions of the present disclosure that include one or more modified AAV capsid proteins are less susceptible to ubiquitination when introduced into a mammalian cell than that of a virion that comprises a corresponding, unmodified, capsid protein.

The present disclosure also concerns rAAV polynucleotide vectors, wherein the nucleic acid segment further comprises a promoter, an enhancer, a post-transcriptional regulatory sequence, a polyadenylation signal, or any combination thereof, operably linked to the nucleic acid segment that encodes the selected polynucleotide of interest.

In some embodiments, the promoter is a heterologous promoter, and in particular, a mammalian PR- or RPE-cell specific promoter.

In certain embodiments, the nucleic acid segments cloned into the novel rAAV expression vectors described herein will express or encode one or more polypeptides, peptides, ribozymes, peptide nucleic acids, siRNA's, RNAi's, antisense oligonucleotides, antisense polynucleotides, antibodies, antigen binding fragments, or any combination thereof when introduced into suitable mammalian host cells, such as PR and/or RPE cells of the human eye.

As noted herein, the therapeutic agents useful in the disclosure may include one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukins, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, chemotherapeutic agents, cytotoxins, or any combination thereof.

The rAAV polynucleotide or nucleic acid vectors of the present disclosure may be comprised within a virion having a serotype that is selected from the group consisting of AAV serotype 1, AAV serotype 2, AAV serotype 3, AAV serotype 4, AAV serotype 5, AAV serotype 6, AAV serotype 7, AAV serotype 8, AAV serotype 9, or AAV serotype 10, or any other serotype as known to one of ordinary skill in the viral arts.

In related embodiments, the disclosure further provides populations and pluralities of rAAV polynucleotide or nucleic acid vectors, virions, infectious viral particles, or host cells that comprise a multi-mutated capsid protein and one or more nucleic acid segments that include an RPE- or a PR-cell-specific promoter operably linked to a selected polynucleotide encoding at least a first diagnostic and/or a first therapeutic molecule.

The disclosure further provides composition and formulations that include one or more of the proteins, nucleic acid segments, viral polynucleotide or nucleic acid vectors, host cells, or viral particles of the present disclosure together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction, and in particular, for delivery of a therapeutic agent to photoreceptors and/or RPE cells of the mammalian eye.

The disclosure further includes a method for providing a mammal in need thereof with a diagnostically- or therapeutically-effective amount of a selected therapeutic agent, the method comprising providing to a cell, tissue or organ of a mammal in need thereof, an amount of one or more of the disclosed rAAV multi-capsid mutant particles or nucleic acid vectors; and for a time effective to provide the mammal with a diagnostically- or a therapeutically-effective amount of the selected therapeutic agent.

The disclosure further provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed rAAV particles or nucleic acid vectors, in an amount and for a time sufficient to diagnose, prevent, treat or ameliorate the one or more symptoms of the disease, disorder, dysfunction, injury, abnormal condition, or trauma in the mammal.

The disclosure also provides a method of transducing a population of mammalian cells, and particular one or more ocular cells in the human eye. In an overall and general sense, the method includes at least the step of introducing into one or more cells of the population, a composition that comprises an effective amount of one or more of the rAAV particles or nucleic acid vectors disclosed herein. In certain embodiments, delivery of the disclosed gene therapy constructs to one or more cells subretinally, permitted the high-efficiency transduction of photoreceptors and RPE cells.

In a further embodiment, the disclosure also provides isolated nucleic acid segments that encode one or more of the AAV mutant capsid proteins as described herein, and provides recombinant nucleic acid vectors comprising said segments.

Additionally, the present disclosure provides compositions, as well as therapeutic and/or diagnostic kits that include one or more of the disclosed AAV particle or nucleic acid vector compositions, formulated with one or more additional ingredients, or prepared with one or more instructions for their use.

The disclosure also demonstrates methods for making, as well as methods of using the disclosed improved rAAV capsid-mutated particles or nucleic acid vectors in a variety of ways, including, for example, ex situ, in vitro and in vivo applications, methodologies, diagnostic procedures, and/or gene therapy methods. Because many of the improved vectors are resistant to proteasomal degradation, they possess significantly increased transduction efficiencies in vivo making them particularly suited for viral vector-based human gene therapy regimens, and for delivering one or more genetic constructs to selected mammalian cells in vivo and/or in vitro.

In one aspect, the disclosure provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the disclosure provide a significant advancement in the art through their use in the treatment, prevention, and/or amelioration of symptoms of one or more mammalian diseases. It is contemplated that human gene therapy will particularly benefit from the present teachings by providing new and improved viral vector constructs for use in the treatment of a number of diverse diseases, disorders, and dysfunctions.

In another aspect, the disclosure concerns modified rAAV vector that encode one or more mammalian therapeutic agents for the prevention, treatment, and/or amelioration of one or more disorders in the mammal into which the vector construct is delivered.

In particular, the disclosure provides rAAV-based expression constructs that encode one or more mammalian therapeutic agent(s) (including, but not limited to, for example, protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In some embodiments, the disclosure provides an rAAV particle that comprises at least a first capsid protein comprising at least a first amino acid substitution to a non-native amino acid at one or more surface exposed amino acid residues in an rAAV capid protein, and wherein the particle further additionally includes a vector comprising at least a first nucleic acid segment that encodes at least a first diagnostic or therapeutic agent operably linked to an RPE- or a PR-cell-specific promoter capable of expressing the segment in one or more cells that have been transformed with the vector. Exemplary PR-cell-specific promoters include, but are not limited to, human rhodopsin kinase (hGRK1), IRBP, rod opsin, NRL, GNAT2e-IRBP, L/M opsin, and cone arrestin promoters. Exemplary RPE-cell-specific promoters include, but are not limited to, VMD2 (Best 1) and RPE65 promoters.

The surface-exposed amino acid-modified rAAV particles or nucleic acid vectors of the present disclosure may optionally further include one or more enhancer sequences that are each operably linked to the nucleic acid segment that encodes the diagnostic or therapeutic molecule of interest. Exemplary enhancer sequences include, but are not limited to, one or more selected from the group consisting of a CMV enhancer, a synthetic enhancer, a photoreceptor-specific-specific enhancer, a retinal pigment epithelial cell-specific enhancer, a vascular-specific enhancer, an ocular-specific enhancer, a neural cell-specific enhancer, a retinal cell-specific enhancer, and such like, and any combination thereof.

Exemplary promoters useful in the practice of the disclosure include, without limitation, one or more tissue-specific promoters, including, for example, but not limited to, photoreceptor specific- and/or RPE cell-specific promoters and the like.

The first nucleic acid segment may also further include one or more post-transcriptional regulatory sequences or one or more polyadenylation signals, including, for example, but not limited to, a woodchuck hepatitis virus post-transcription regulatory element (WRPE), a polyadenylation signal sequence, or an intron/exon junctions/splicing signals, or any combination thereof.

Exemplary diagnostic or therapeutic agents deliverable to host cells by the present vector constructs include, but are not limited to, an agent selected from the group consisting of a polypeptide, a peptide, an antibody, an antigen binding fragment, a ribozyme, a peptide nucleic acid, a siRNA, an RNAi, an antisense oligonucleotide, an antisense polynucleotide, and any combination thereof.

In exemplary embodiments, the improved rAAV vectors of the disclosure will encode at least one diagnostic or therapeutic protein or polypeptide selected from the group consisting of a molecular marker, photosensitive opsins, including, without limitation, rhodopsin, melanopsin, cone opsins, channel rhodopsins, bacterial or archea-associated opsins, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In some embodiments, the capsid-modified rAAV vectors of the present disclosure may include one or more nucleic acid segments that encode a polypeptide selected from the group consisting of RPE65, Bestrophin (BEST1), REP1, MERTK, SOD2, MYO7A, MFRP, LRAT, KCNJ13, ornithine aminotransferase (OAT), and any combination or peptide fragment thereof.

In some embodiments, the capsid-modified rAAV vectors of the present disclosure may include one or more nucleic acid segments that encode a polypeptide selected from the group consisting of CNTF, GDNF, BDNF, IL6, LIF, XIAP, STAT3, and any combination or peptide fragment thereof.

In certain applications, the capsid-modified rAAV vectors of the present disclosure may include one or more nucleic acid segments that encode a polypeptide selected from the group consisting of nyctalopin (nyx), metabotropic glutamate receptor 6-mGluR6 (Grm6), transient receptor potential melastatin 1 (TRPM1), G protein coupled receptor 179 (GPR179), and G proteins, $G\beta5$, $G\beta3$, $G\alpha0_{1/2}$, $G\gamma13$, RGS7, RGS11, R9AP, and any combination or peptide fragment thereof.

In another embodiment, the disclosure concerns genetically-modified improved transduction-efficiency rAAV nucleic acid vectors that include at least a first nucleic acid segment that encodes one or more diagnostic or therapeutic agents that alter, inhibit, reduce, prevent, eliminate, or impair the activity of one or more endogenous biological processes in a mammalian cell suitably transformed with the vector of interest. In certain embodiments, such diagnostic or therapeutic agents may include a molecule that selectively inhibits or reduces the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

The genetically-modified rAAV nucleic acid vectors and expression systems of the present disclosure may also further include a second nucleic acid segment that comprises, consists essentially of, or consists of, one or more enhancers, one or more regulatory elements, one or more transcriptional elements, or any combination thereof, that alter, improve, regulate, and/or affect the transcription of the nucleotide sequence of interest expressed by the modified rAAV vectors.

For example, the rAAV nucleic acid vectors of the present disclosure may further include a second nucleic acid segment that comprises, consists essentially of, or consists of, a CMV enhancer, a synthetic enhancer, a cell-specific enhancer, a tissue-specific enhancer, or any combination thereof. The second nucleic acid segment may also further comprise, consist essentially of, or consist of, one or more intron sequences, one or more post-transcriptional regulatory elements, or one or more enhancers from rhodopsin, melanopsin, cone opsins, channel rhodopsins, bacterial or archea-associated opsins, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neuropilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinsase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, or a tumor suppressor. The second nucleic acid segment may also further comprise, consist essentially of, or consist of, one or more intron sequences, one or more post-transcriptional regulatory elements, or one or more enhancers from RPE65, Bestrophin (BEST1), REP1, MERTK, SOD2, MYO7A, MFRP, LRAT, KCNJ13, or ornithine aminotransferase (OAT). The second nucleic acid segment may also further comprise, consist essentially of, or consist of, one or more intron sequences, one or more post-transcriptional regulatory elements, or one or more enhancers from RPE65, Bestrophin (BEST1), REP1, MERTK, SOD2, MYO7A, MFRP, LRAT, KCNJ13, ornithine aminotransferase (OAT), CNTF, GDNF, BDNF, IL6, LIF, XIAP, or STAT3.

The improved vectors and expression systems of the present disclosure may also optionally further include a polynucleotide that comprises, consists essentially of, or consists of, one or more polylinkers, restriction sites, and/or multiple cloning region(s) to facilitate insertion (cloning) of one or more selected genetic elements, genes of interest, and/or one or more therapeutic or diagnostic molecules into the rAAV vector at a selected site within the vector.

In further aspects of the present disclosure, the exogenous polynucleotide(s) that may be delivered into suitable host cells by the improved, capsid-modified, rAAV particles comprising nucleic acid vectors disclosed herein are of mammalian origin, with polynucleotides encoding one or more polypeptides or peptides of, e.g., human, non-human primate, porcine, bovine, ovine, feline, canine, equine, epine, caprine, or lupine origin.

The exogenous polynucleotide(s) that may be delivered into host cells by the disclosed capsid-modified particles or viral vectors may, in certain embodiments, encode one or more proteins, one or more polypeptides, one or more peptides, one or more enzymes, or one or more antibodies (or antigen-binding fragments thereof), or alternatively, may express one or more siRNAs, ribozymes, antisense oligonucleotides, PNA molecules, or any combination thereof. When combinational gene therapies are desired, two or more different molecules may be produced from a single rAAV expression system, or alternatively, a selected host cell may be transfected with two or more unique rAAV expression systems, each of which may comprise one or more distinct polynucleotides that encode a therapeutic agent.

In other embodiments, the disclosure also provides rAAV nucleic vectors that are comprised within an infectious adeno-associated viral particle or a virion, as well as pluralities of such virions or infectious particles. Such vectors and virions may be comprised within one or more diluents, buffers, physiological solutions or pharmaceutical vehicles, or formulated for administration to a mammal in one or more diagnostic, therapeutic, and/or prophylactic regimens. The vectors, virus particles, virions, and pluralities thereof of the present disclosure may also be provided in excipient formulations that are acceptable for veterinary administration to selected livestock, exotics, domesticated animals, and companion animals (including pets and such like), as well as to non-human primates, zoological or otherwise captive specimens.

The disclosure also concerns host cells that comprise at least one of the disclosed capsid protein-modified particles or rAAV expression vectors. Such host cells are particularly mammalian host cells, such as human retinal cells, and may be either isolated, in cell or tissue culture. In the case of genetically modified animal models, the transformed host cells may even be comprised within the body of a non-human animal itself.

In certain embodiments, the creation of recombinant non-human host cells, and/or isolated recombinant human host cells that comprise one or more of the disclosed rAAV nucleic acid vectors is also contemplated to be useful for a variety of diagnostic, and laboratory protocols, including, for example, means for the production of large-scale quantities of the rAAV vectors described herein. Such virus production methods are particularly contemplated to be an improvement over existing methodologies including in particular, those that require very high titers of the viral stocks in order to be useful as a gene therapy tool. The inventors contemplate that one very significant advantage of the present methods will be the ability to utilize lower titers of viral particles in mammalian transduction protocols, yet still retain transfection rates at a suitable level.

Compositions comprising one or more of the disclosed capsid-modified, improved transduction-efficiency rAAV vectors, expression systems, infectious AAV particles, or host cells also form part of the present disclosure, and particularly those compositions that further comprise at least a first pharmaceutically-acceptable excipient for use in therapy, and for use in the manufacture of medicaments for the treatment of one or more mammalian diseases, disorders, dysfunctions, or trauma. Such pharmaceutical compositions may optionally further comprise one or more diluents, buffers, liposomes, a lipid, a lipid complex. Alternatively, the surface exposed amino acid-substituted rAAV vectors of the present disclosure may be comprised within a plurality of microspheres, nanoparticles, liposomes, or any combination thereof. Pharmaceutical formulations suitable for intravitreal or subretinal administration to one or both eyes of a human or other mammal are contemplated, however, the compositions disclosed herein may also find utility in administration to discreet areas of the mammalian body, including for example, formulations that are suitable for direct injection into one or more organs, tissues, or cell types in the body.

Other aspects of the disclosure concern recombinant adeno-associated virus virion particles (e.g., capsid-modified, improved transduction efficiency particles), compositions, and host cells that comprise, consist essentially of, or consist of, one or more of the rAAV vectors disclosed herein, such as for example pharmaceutical formulations of the vectors intended for intravitreal or subretinal administration to a mammalian eye.

Kits comprising one or more of the disclosed capsid-modified rAAV particles or nucleic acid vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Another important aspect of the present disclosure concerns methods of use of the disclosed rAAV particles or vectors, virions, expression systems, compositions, and host cells described herein in the preparation of medicaments for diagnosing, preventing, treating or ameliorating at least one or more symptoms of a disease, a dysfunction, a disorder, an abnormal condition, a deficiency, injury, or trauma in an animal, and in particular, in the eye of a vertebrate mammal. Such methods generally involve direct administration to the vitreous of one or both eyes of a mammal in need thereof, one or more of the disclosed vectors, virions, viral particles, host cells, compositions, or pluralities thereof, in an amount and for a time sufficient to diagnose, prevent, treat, or lessen one or more symptoms of such a disease, dysfunction, disorder, abnormal condition, deficiency, injury, or trauma in one or both eyes of the affected animal. The methods may also encompass prophylactic treatment of animals suspected of having such conditions, or administration of such compositions to those animals at risk for developing such conditions either following diagnosis, or prior to the onset of symptoms.

As described above, in some embodiments, the exogenous polynucleotide will encode one or more therapeutic proteins, polypeptides, peptides, ribozymes, or antisense oligonucleotides, or a combination of these. In fact, the exogenous polynucleotide may encode two or more such molecules, or a plurality of such molecules as may be desired. When combinational gene therapies are desired, two or more different molecules may be produced from a single rAAV expression system, or alternatively, a selected host cell may be transfected with two or more unique rAAV expression systems, each of which will provide unique heterologous polynucleotides encoding at least two different such molecules.

Compositions comprising one or more of the disclosed rAAV vectors, expression systems, infectious AAV particles, host cells also form part of the present disclosure, and particularly those compositions that further comprise at least a first pharmaceutically-acceptable excipient for use in the manufacture of medicaments and methods involving therapeutic administration of such rAAV particles or nucleic acid vectors. In some embodiments, pharmaceutical formulations are suitable for intravitreal or subretinal administration into one or both eyes of a human or other mammal.

Another important aspect of the present disclosure concerns methods of use of the disclosed particles, vectors, virions, expression systems, compositions, and host cells described herein in a method for treating or ameliorating the symptoms or in the preparation of medicaments for treating or ameliorating the symptoms of various deficiencies in an eye of a mammal, and in particular one or more deficiencies in human photoreceptors or RPE cells. Exemplary diseases and disorders of the eye (e.g., caused by one or more genetic deficiencies in a PR or PRE cell) for treatment or amelioration of symptoms include Retinitis pigmentosa, Leber Congenital Amaurosis, Age Related Macular Degeneration, Best disease, Stargardts disease, Usher Syndrome, Geographic Atrophy, Diabetic Retinopathy, Retinoschisis, Achromatopsia, Choroideremia, Bardet Biedl Syndrome, and glycogen storage diseases (ocular manifestation). Such methods generally involve intravitreal or subretinal administration to one or both eyes of a subject in need thereof, one or more of the disclosed particles vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

rAAV Vectors

Recombinant adeno-associated virus (rAAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, i.e., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and $CD8^+$ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007). These results suggested that immune responses remain a concern for AAV vector-mediated gene transfer.

Adeno-associated virus (AAV) is considered the optimal vector for ocular gene therapy due to its efficiency, persistence and low immunogenicity (Daya and Berns, 2008). Identifying vectors capable of transducing PRs via the vitreous has historically relied on identifying which serotypes have native tropism for this cell type following local delivery. Several serotypes have been used to successfully target transgene to PRs following subretinal injection (including, e.g., AAV2, AAV5 and AAV8) with all three demonstrating efficacy in experiments performed across multiple mammalian species (e.g., mouse, rat, dog, pig and non-human primate) (Ali et al., 1996; Auricchio et al., 2001; Weber et al., 2003; Yang et al., 2002; Acland et al., 2001; Vandenberghe et al., 2011; Bennett et al., 1999; Allocca et al., 2007; Petersen-Jones et al., 2009; Lotery et al., 2003; Boye et al., 2012; Stieger et al., 2008; Mussolino et al., 2011; Vandenberghe et al., 2011).

Studies comparing their relative efficiency following subretinal delivery in the rodent show that both AAV5 and AAV8 transduce PRs more efficiently than AAV2, with AAV8 being the most efficient (Yang et al., 2002; Allocca et al., 2007; Rabinowitz et al., 2002; Boye et al., 2011; Pang et al., 2011). It was previously shown that AAV2 and AAV8 vectors containing point mutations of surface-exposed tyrosine residues (tyrosine to phenylalanine, Y–F) display increased transgene expression in a variety of retinal cell types relative to unmodified vectors following both subretinal and intravitreal injection (Petrs-Silva et al., 2009; Petrs-Silva et al., 2011). Of the vectors initially tested by those authors, an AAV2 triple mutant (designated "triple Y→F") exhibited the highest transduction efficiency following intravitreal injection, whereas an AAV2 quadruple mutant ("quad Y→F") exhibited the novel property of enhanced transduction of outer retina (Petrs-Silva et al., 2011).

Further improvements in transduction efficiency have been achieved via directed mutagenesis of surface-exposed threonine (T) or serine (S) residues to non-native amino acids at one of more of those amino acids. Both Y→F and T→V/T→A mutations have been shown to increase efficiency by decreasing phosphorylation of capsid and subsequent ubiquitination as part of the proteosomal degradation pathway (Zhong et al., 2008; Aslanidi et al., In Press; Gabriel et al., 2013). It has been found that the transduction profile of intravitreally-delivered AAV is heavily dependent upon the injection procedure itself. Due to the small size of the mouse eye, it is not uncommon for trans-scleral, intravitreal injections to result in damage to the retina that might allow delivery of some vector directly to the subretinal space.

In some embodiments, a rAAV nucleic acid vector described herein comprises inverted terminal repeat sequences (ITRs), such as those derived from a wild-type AAV genome, such as the AAV2 genome. In some embodiments, the rAAV nucleic acid vector further comprises a transgene (also referred to as a heterologous nucleic acid molecule) operably linked to a promoter and optionally, other regulatory elements, wherein the ITRs flank the transgene. In some embodiments, the promoter is a PR- or RPE-cell-specific promoter. In some embodiments, the transgene encodes a therapeutic agent or diagnostic agent of interest. In some embodiments, the rAAV nucleic acid vector is encapsidated by a rAAV particle as described herein, e.g., comprising a modified capsid protein. Exemplary modified capsid proteins (e.g., modified AAV2 capsid proteins) of the present disclosure include, but are not limited to, those comprising three, four, five, six, or seven or more non-native amino acid substitutions at three, four, five, six, or seven or more amino acid residues selected from the group consisting of: (a) Tyr444, Arg487, Thr491, Tyr500, Glu530, Arg585, Arg588, and Tyr730 of the wild-type AAV2 capsid protein as set forth in SEQ ID NO:2; and (b) three, four, five, six, or seven or more non-native amino acid substitutions at three, four, five, six, or seven or more equivalent amino acid positions corresponding thereto, in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof. The non-native amino acid substitutions may be any amino acid residue other than the native residue. In some embodiments, the non-native amino acid substitution is a non-conservative amino acid substitution. In some embodiments, the non-native amino acid substitution is an alanine or glycine. In some embodiments, the non-native amino acid substitution is a phenylalanine, valine, serine, threonine or glycine. In some embodiments, the modified capsid protein (e.g., modified AAV2 capsid protein) comprises or consists of the substitutions Y444F, Y500F, Y730F, T491V, R585S, R588T, and R487G in the wild-type AAV2 capsid protein, e.g., as set forth in SEQ ID NO:2.

Exemplary rAAV nucleic acid vectors useful according to the disclosure include single-stranded (ss) or self-complementary (sc) AAV nucleic acid vectors, such as single-stranded or self-complementary recombinant viral genomes.

Methods of producing rAAV particles and nucleic acid vectors are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid containing the nucleic acid vector sequence may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the one or more helper plasmids includes a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV2 and includes modifications to the gene in order to produce a modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

Uses for Improved, Capsid-Modified rAAV Vectors

The present disclosure provides compositions including one or more of the disclosed surface exposed amino acid capsid-modified rAAV particles or vectors comprised within a kit for diagnosing, preventing, treating or ameliorating one or more symptoms of a mammalian disease, injury, disorder, trauma or dysfunction. Such kits may be useful in diagnosis, prophylaxis, and/or therapy, and particularly useful in the treatment, prevention, and/or amelioration of one or more defects in the mammalian eye as discussed herein.

The disclosure also provides for the use of a composition disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction.

Likewise, the disclosure also provides a method for treating or ameliorating the symptoms of such a disease, injury, disorder, or dysfunction in one or both eyes of a mammal, and of a human in particular. Such methods generally involve at least the step of administering to a mammal in need thereof, one or more of the multi-surface exposed amino acid residue substituted, VP3 capsid protein-modified rAAV particles as disclosed herein, in an amount and for a time sufficient to treat or ameliorate the symptoms of such a disease, injury, disorder, or dysfunction in one or both eyes of the mammal.

The disclosure also provides a method for providing to a mammal in need thereof, a therapeutically-effective amount of the rAAV compositions of the present disclosure, in an amount, and for a time effective to provide the patient with a therapeutically-effective amount of the desired therapeutic agent(s) encoded by one or more nucleic acid segments comprised within the rAAV nucleic acid vector. In some embodiments, the therapeutic agent is selected from the group consisting of a polypeptide, a peptide, an antibody, an antigen-binding fragment, a ribozyme, a peptide nucleic acid, an siRNA, an RNAi, an antisense oligonucleotide, an antisense polynucleotide, a diagnostic marker, a diagnostic molecule, a reporter molecule, and any combination thereof.

Pharmaceutical Compositions Comprising Capsid-Mutated rAAV Vectors

One important aspect of the present methodology is the fact that the improved rAAV particles described herein permit the delivery of smaller titers of viral particles in order to achieve the same transduction efficiency as that obtained using higher levels of conventional, non-surface capsid modified rAAV particles. To that end, the amount of AAV compositions and time of administration of such compositions will be within the purview of the skilled artisan having benefit of the present teachings. In fact, the inventors contemplate that the administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or over a relatively prolonged period, as may be determined by the medical practitioner overseeing the administration of such compositions.

For example, the number of infectious particles administered to a mammal may be approximately $10^7$, $10^8$, $10^9$, $10^{10}$, $10^{11}$, $10^{12}$, $10^{13}$, or even higher, infectious particles/mL, given either as a single dose (or divided into two or more administrations, etc.,) as may be required to achieve therapy of the particular disease or disorder being treated. In fact, in certain embodiments, it may be desirable to administer two or more different rAAV particle- or vector-based compositions, either alone, or in combination with one or more other diagnostic agents, drugs, bioactives, or such like, to achieve the desired effects of a particular regimen or therapy. In most rAAV-vectored, gene therapy-based regimens, the inventors contemplate that lower titers of infectious particles will be required when using the modified-capsid rAAV particles described herein, as compared to the use of equivalent wild-type, or corresponding "un-modified" rAAV particles.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

To express a therapeutic agent in accordance with the present disclosure one may prepare a capsid-modified rAAV particle that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded polypeptide. This is the meaning of "recombinant expression" in this context. In some embodiments, recombinant vector constructs are those that include a capsid-protein modified rAAV vector that contains an RPE cell- or a photoreceptor cell-specific promoter, operably linked to at least one nucleic acid segment encoding one or more diagnostic, and/or therapeutic agents. Such vectors are described in detail herein.

When the use of such vectors is contemplated for introduction of one or more exogenous proteins, polypeptides, peptides, ribozymes, and/or antisense oligonucleotides, to a particular cell transfected with the vector, one may employ the capsid-modified rAAV vectors disclosed herein to deliver one or more exogenous polynucleotides to a selected host cell, e.g., to one or more selected cells within the mammalian eye.

The genetic constructs of the present disclosure may be prepared in a variety of compositions, and may be formulated in appropriate pharmaceutical vehicles for administration to human or animal subjects. The rAAV particle- and vector-based constructs of the present disclosure provide new and useful therapeutics for the treatment, control, and amelioration of symptoms of a variety of disorders, diseases, injury, and/or dysfunctions of the mammalian eye, and in particular inherited diseases involving mutations in one or more PR- or RPE-specific proteins.

In some embodiments, the number of viral particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, viral particles of higher than $10^{13}$ particles/ml may be administered. In some embodiments, the number of viral particles administered to a subject may be on the order ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, viral particles of higher than $10^{13}$ vgs/ml are be administered. The viral particles can be administered as a single dose, or divided into two or more administrations as may be required to achieve therapy of the particular disease or disorder being treated. In some embodiments, 0.0001 ml to 10 mls, e.g., 0.001 ml, 0.01 ml, 0.1 ml, 1 ml, 2 ml, 5 ml or 10 ml, are delivered to a subject.

In some embodiments, the disclosure provides formulations of one or more viral-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particles described herein may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravitreal, intraocular, intravenous, intranasal, intra-articular, and intramuscular administration and formulation.

Typically, these formulations may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver rAAV particles in suitably formulated pharmaceutical compositions disclosed herein either subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection. The pharmaceutical forms of the compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be administered to the subject being treated by standard routes including, but not limited to, pulmonary, intranasal, oral, inhalation, parenteral such as intravenous, topical, transdermal, intradermal, transmucosal, intraperitoneal, intramuscular, intracapsular, intraorbital, intravitreal, intracardiac, transtracheal, subcutaneous, subcuticular, intraarticular, subcapsular, subarachnoid, intraspinal, epidural and intrasternal injection.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage may occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the rAAV particles in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, exemplary methods of preparation are vacuum-drying and freeze-drying techniques which yield a powder of the active ingredient plus any additional desired ingredient from a previously sterile-filtered solution thereof.

The amount of rAAV particle compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of viral particles to provide therapeutic benefit to the patient undergoing such treatment. Alternatively, in some circumstances, it may be desirable to provide multiple, or successive administrations of the compositions, either over a relatively short, or a relatively prolonged period of time, as may be determined by the medical practitioner overseeing the administration of such compositions.

The composition may include rAAV particles or nucleic acid vectors either alone, or in combination with one or more additional active ingredients, which may be obtained from natural or recombinant sources or chemically synthesized.

Exemplary Definitions

In accordance with the present disclosure, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this disclosure belongs. Although any methods and compositions similar or equivalent to those described herein can be used in the practice or testing of the present disclosure, the preferred methods and compositions are described herein. For purposes of the present disclosure, the following terms are defined below:

The term "subject," as used herein, describes an organism, including mammals such as primates, to which treatment with the compositions according to the present disclosure can be provided. Mammalian species that can benefit from the disclosed methods of treatment include, but are not limited to, apes; chimpanzees; orangutans; humans; monkeys; domesticated animals such as dogs and cats; livestock such as horses, cattle, pigs, sheep, goats, and chickens; and other animals such as mice, rats, guinea pigs, and hamsters.

The term "treatment" or any grammatical variation thereof (e.g., treat, treating, and treatment etc.), as used herein, includes but is not limited to, alleviating a symptom of a disease or condition; and/or reducing, suppressing, inhibiting, lessening, ameliorating or affecting the progression, severity, and/or scope of a disease or condition.

The term "effective amount," as used herein, refers to an amount that is capable of treating or ameliorating a disease or condition or otherwise capable of producing an intended therapeutic effect.

The term "promoter," as used herein refers to a region or regions of a nucleic acid sequence that regulates transcription.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

EXEMPLARY EMBODIMENTS

Exemplary, non-limiting embodiments are provided below.

Embodiment 1

A recombinant adeno-associated viral (rAAV) vector comprising: a polynucleotide that encodes a modified capsid protein, wherein the modified capsid protein comprises at least a first non-native amino acid at a position that corresponds to a surface-exposed amino acid residue in the wild-type AAV2 capsid protein, and further wherein the transduction efficiency of a virion comprising the modified capsid protein is higher than that of a virion comprising a corresponding, unmodified wild-type capsid protein, and wherein the polynucleotide further comprises a nucleic acid segment that encodes a diagnostic or therapeutic molecule operably linked to a promoter that is capable of expressing the nucleic acid segment in one or more photoreceptors or retinal pigment epithelial cells of a mammalian eye, wherein the modified capsid protein comprises three or more non-native amino acid substitutions at positions corresponding to three distinct surface-exposed amino acid residues of the wild-type AAV2 capsid protein as set forth in SEQ ID NO:2; or to three distinct surface-exposed amino acid residues corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

Embodiment 2

The rAAV vector of embodiment 1, wherein the non-native amino acid substitutions occur at amino acid residues: (a) Y444, Y500, and Y730; (b) Y272, Y444, Y500, and Y730; (c) Y444, T491, Y500, R585, R588, R487, and Y730; (d) Y444, T491, Y500, R585, and Y730; (e) Y444, T491, Y500, R588, and Y730; (f) Y444, T491, Y500, R585, R588, and Y730; (g) Y444, T491, Y500, and Y730; (h) Y444, T491, Y500, E530, R585, R588, R487, and Y730; (i) Y444, T491, Y500, E530, R585, and Y730; (j) Y444, T491, Y500, E530, R588, and Y730; (k) Y444, T491, Y500, E530, R585, R588, and Y730; or (l) Y444, T491, Y500, E530, and Y730; of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

Embodiment 3

The rAAV vector of embodiment 2, wherein the non-native amino acid substitutions comprise: (a) Y444F, Y500F, and Y730F; (b) Y272F, Y444F, Y500F, and Y730F; (c) Y444F, T491V, Y500F, R585S, R588T, R487G, and Y730F; (d) Y444F, T491V, Y500F, R585S, and Y730F; (e) Y444F, T491V, Y500F, R588T, and Y730F; (f) Y444F, T491V, Y500F, R585S, R588T, and Y730F; (g) Y444F, T491V, Y500F, and Y730F; (h) Y444F, T491V, Y500F, E530K, R585S, R588T, R487G, and Y730F; (i) Y444F, T491V, Y500F, E530K, R585S, and Y730F; (j) Y444F, T491V, Y500F, E530K, R588T, and Y730F; (k) Y444F, T491V, Y500F, E530K, R585S, R588T, and Y730F; or (l) Y444F, T491V, Y500F, E530K, and Y730F; of the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10, or any combination thereof.

Embodiment 4

The rAAV vector of embodiment 1, wherein the transduction efficiency of a virion comprising the modified vector is about 2- to about 50-fold higher in the one or more photoreceptor or RPE cells than that of a virion that comprises a corresponding, unmodified, wild-type capsid protein.

Embodiment 5

The rAAV vector of embodiment 1, wherein the nucleic acid segment further comprises an enhancer, a post-transcriptional regulatory sequence, a polyadenylation signal, or any combination thereof, operably linked to the nucleic acid segment encoding the therapeutic agent.

Embodiment 6

The rAAV vector of embodiment 1, wherein the nucleic acid segment expresses or encodes in one or more photoreceptor cells or RPE cells of a mammalian eye, a polypeptide, a peptide, a ribozyme, a peptide nucleic acid, an siRNA, an RNAi, an antisense oligonucleotide, an antisense polynucleotide, an antibody, an antigen binding fragment, or any combination thereof.

Embodiment 7

A method for providing a mammal in need thereof with a therapeutically-effective amount of a selected therapeutic agent, the method comprising administering to one or both eyes of the mammal, an amount of the rAAV vector of embodiment 1; and for a time effective to provide the mammal with a therapeutically-effective amount of the selected therapeutic agent.

Embodiment 8

The method of embodiment 7, wherein the method comprises intravitreally or sub-retinally administering to one or both eyes of the mammal, an amount of the rAAV vector of embodiment 1; and for a time effective to provide the mammal with a therapeutically-effective amount of the selected therapeutic agent.

Embodiment 9

A method for treating or ameliorating one or more symptoms of a disease, a disorder, a dysfunction, an injury, an abnormal condition, or trauma in a mammal, the method comprising, intravitreally administering to one or both eyes of the mammal in need thereof, the rAAV vector of embodiment 1, in an amount and for a time sufficient to treat or ameliorate the one or more symptoms of the disease, the disorder, the dysfunction, the injury, the abnormal condition, or the trauma in the mammal.

Embodiment 10

A method for expressing a nucleic acid segment in one or more photoreceptor cells or one or more RPE cells of a mammal, the method comprising: subretinally or intravitreally administering to one or both eyes of the mammal the rAAV vector of embodiment 1, wherein the polynucleotide further comprises at least a first polynucleotide that comprises a PR- or an RPE-cell-specific promoter operably linked to at least a first nucleic acid segment that encodes a therapeutic agent, for a time effective to produce the therapeutic agent in the one or more PR cells or RPE cells of the mammal.

Embodiment 11

The method of embodiment 10, wherein the mammal is human.

Embodiment 12

The method of embodiment 11, wherein the human is a neonate, a newborn, an infant, or a juvenile.

Embodiment 13

The method of embodiment 11, wherein the human has, is suspected of having, is at risk for developing, or has been diagnosed with a retinal disorder, a retinal disease, a retinal dystrophy, or any combination thereof.

Embodiment 14

The method of embodiment 11, wherein the retinal disorder, retinal disease, or retinal dystrophy is inheritable.

Embodiment 15

The method of embodiment 11, wherein production of the therapeutic agent a) preserves one or more photoreceptor cells or one or more RPE cells, b) restores one or more rod- and/or cone-mediated functions, c) restores visual behavior in one or both eyes, or d) any combination thereof.

Embodiment 16

The method of embodiment 11, wherein production of the therapeutic agent persists in the one or more photoreceptor cells or the one or more RPE cells substantially for a period of at least three months following an initial administration of the rAAV vector into the one or both eyes of the mammal.

Embodiment 17

The method of embodiment 16, wherein production of the therapeutic agent persists in the one or more retinal cells substantially for a period of at least six months following an initial administration of the rAAV vector into the one or both eyes of the mammal.

Embodiment 18

The method of embodiment 10, wherein the vector is a self-complementary rAAV (scAAV).

Embodiment 19

The method of embodiment 10, wherein the vector is provided to the one or both eyes by administration of an infectious adeno-associated viral particle, an rAAV virion, or a plurality of infectious rAAV particles.

Embodiment 20

The method of embodiment 10, wherein the therapeutic agent is an agonist, an antagonist, an anti-apoptosis factor, an inhibitor, a receptor, a cytokine, a cytotoxin, an erythropoietic agent, a glycoprotein, a growth factor, a growth factor receptor, a hormone, a hormone receptor, an interferon, an interleukin, an interleukin receptor, a nerve growth factor, a neuroactive peptide, a neuroactive peptide receptor, a protease, a protease inhibitor, a protein decarboxylase, a protein kinase, a protein kinsase inhibitor, an enzyme, a receptor binding protein, a transport protein or an inhibitor thereof, a serotonin receptor, or an uptake inhibitor thereof, a serpin, a serpin receptor, a tumor suppressor, a chemotherapeutic, or any combination thereof.

EXAMPLES

Example 1—Highly-Selective Transduction of PRs and RPE Cells Following

Subretinal Delivery of Capsid-Mutated rAAV Vectors

The majority of inherited retinal diseases are caused by mutations in genes expressed within photoreceptors (PRs) and retinal pigment epithelium (RPE). A key goal of the present disclosure was the development of rAAV particles that could efficiently transduce and deliver therapeutic transgene in a rAAV nucleic acid vector to one or both cell types at transduction efficiencies, and/or tissue specificities that were greater than that of the wild-type, unmodified particles. In exemplary embodiments, improved serotype 2-based AAV particles were developed and tested in vitro and/or in vivo.

These 'second-generation' rAAV capsid-mutated particles improve transduction of PRs and RPE by enhancing the ability of vector to deliver its cargo to the nucleus. In illustrative examples, such improved particles were created by mutating several tyrosine residues on the vector's capsid surface to non-native amino acids. For example, in some embodiments, a triple mutant rAAV particles was developed that contained three tyrosine-to-phenylalanine (Y→F) mutations at residues 444, 500 and 730 of the wild-type AAV2 protein. The resulting particle showed significantly increased transduction relative to the native, unmodified AAV2 particle, from which the mutant was derived.

This exemplary particle, designated AAV2(Y444F+Y500F+Y730F), and which was given the shorthand notation "AAV2(tripleY→F)" displayed increased transduction efficiency in a variety of cell lines both in vitro, and also in multiple tissues in vivo as compared to the wild-type, unmodified AAV2 particle. The addition of a threonine-to-valine (T→V) mutation at residue 491 in the AAV2(tripleY→F) particle further improved in vitro and in vivo performance, resulting in the creation of a 'third-generation' quad-mutated AAV2 particle, which the inventors designated AAV2(tripleY→F+T491V), and also referred to herein by its shorthand notation as "AAV2MAX." The improved performances of both classes of these particles and nucleic acid vectors contained within these particles was a result of their enhanced ability to traffic to the nucleus and unload their "cargo" as compared to wild-type AAV2 particles, whose unmodified tyrosine and threonine residues serve as signals for proteosomal degradation.

A further series of novel AAV2-based particles were also constructed and evaluated for their ability to transduce photoreceptors and RPE cells following intravitreal injection in a murine model. The inventors demonstrated that the ability of these capsid-mutant particles to transduce neural retina depended on their ability to bind to heparan sulfate (HS) proteoglycan in the inner limiting membrane (ILM), a typical basement membrane that forms the vitreoretinal junction. Because the primary cellular receptor for AAV2 is HS, vectors based on this serotype exhibit significantly improved transduction relative to other serotypes such as AAV5, which binds sialic acid (a component that is absent from the ILM).

By comparing the transduction profiles of various Y→F/T→V capsid mutated AAV2 particles following intravitreal injection in mice, and by subsequently analyzing the respective affinities for HS (using chromatography on heparin agarose columns), the inventors confirmed that each capsid's affinity for HS dictated the resulting particle's transduction profile. It was discovered that the more tightly it bound, the less the particle 'penetrated' through the retina and vice-versa. Simply stated, in order to transduce PRs and RPE from the vitreous, these vectors must effectively bind HS (to bind to the ILM), but not so strongly that they remain sequestered there. Exemplary AAV2 variants that primarily transduced inner retina from the vitreous (e.g., AAV2 wt and AAV2tripleY→F) had very strong affinity for HS, while those vectors that transduced photoreceptors (e.g., AAV2quadY→F and AAV2quadY→F+T→V) had only moderate affinity.

With this information, an additional set of 'fourth-generation' capsid variants was also developed using the AAV2MAX vector as a template. Structure-informed mutations of known HS binding residues on the AAV2 capsid were made, to generate vectors demonstrating a range of HS affinities (or, in certain mutants, no affinity for HS whatsoever). One such construct, a heptuple AAV2 mutant, designated AAV2(Y444F+Y500F+Y730F+T491V+R585S+R588T+R487G, and which has been given the shorthand notation "AAV2MAXΔHS" had essentially no HS affinity. As predicted, this vector did not transduce cells in vitro or in retina in vivo, when delivered by intravitreal injection. Surprisingly, however, when the AAV2MAXΔHS vector was delivered sub-retinally, it was highly efficient at transducing PRs and RPE cells.

In fact, the levels of transgene expression mediated by the fourth-generation particle, AAV2MAXΔHS were about that achieved using serotypes such as AAV5, which are well established in the scientific literature as being 'photoreceptor-phillic.' Importantly, in the AAV2MAXΔHS-based particles, photoreceptor transduction occurred in the absence of HS binding. Therefore, without wishing to be bound by theory, another ligand-receptor pair may be responsible for attachment of vectors such as AAV2MAXΔHS to the surface of photoreceptors. The inventors reasoned that it was likely the residues responsible for this pairing were "unmasked" by mutation of the canonical HS binding footprint.

It was reasoned that rAAV particles created using the AAV2MAXΔHS "backbone," as well as analogous constructs that exhibited a reduced or impaired binding to HS, could serve as useful alternatives to conventional AAV5- or AAV8-serotype-based vectors for the efficient delivery of transgene to photoreceptors following subretinal injection.

To test this theory, a further three exemplary AAV2MAXΔHS-based capsid-mutated particles were created, including:
AAV2(Y444F+Y500F+Y730F+T491V+R585S),
AAV2(Y444F+Y500F+Y730F+T491V+R588T), and
AAV2(Y444F+Y500F+Y730F+T491V+R585S+R588T).
Each of these particles demonstrated a modified affinity for HS, and were predicted to recapitulate the ability to transduce PRs and RPE from the vitreous as seen with vectors such as AAV2(quadY→F) and AAV2(quadY→F+

T→V), while still maintaining the maximal post-cellular entry efficiencies of the AAV2MAX-based particle constructs.

The inventors have also created another modified rAAV2 particle construct that was synthesized from AAV2MAXΔHS. This variant contained an E→K mutation at amino acid position 530, which is outside the AAV2 HS binding footprint. Analysis of the AAV2MAXΔHS+E530K construct is expected to show a restored HS affinity, though not interfering with the new receptor-ligand footprint that was unmasked in the ΔHS family of mutants.

Example 2—Heparan Sulfate Affinity Dictates Transduction of PRs from the Vitreous by Capsid Mutated AAV2 Variants Developing AAV particles capable of efficiently transducing retina from the vitreous provides a major step forward in translating gene therapy to the clinic. It is known that mutagenesis of surface exposed tyrosine residues prevents proteosomal degradation and increases nuclear transport of AAV thereby increasing its transduction efficiency. A variant with four Y→F mutations, AAV(quadY→F), transduced distal layers of the retina, including photoreceptors, when delivered to the vitreous. The primary cellular receptor for AAV2 is heparan sulfate (HS), and heparan sulfate proteoglycan (HSPG) is a primary component of the inner limiting membrane. The inventors hypothesized that the relative 'penetrating' ability of capsid mutants relies on their respective HS affinities.

Methods:

AAV2 based particles containing mutated capsids containing combinations of Y→F and/or T→V mutations were analyzed by chromatography on heparin agarose columns to determine respective affinities. A new set of capsid variants was created using a triple Y→F/single T→V variant (AAV2MAX) as template. Structure informed mutations of the known HS binding residues of AAV2 were performed with the goal of generating vectors with a range of HS binding or no binding whatsoever (AAV2MAXΔHS). These and related variants are being evaluated for transduction efficiencies in vitro and in vivo, via subretinal and intravitreal injections in a murine animal model.

Results:

AAV2 variants that primarily transduce inner retina from the vitreous (AAV2 wt and AAV2tripleY→F) have strong affinity for HS, while those that transduce photoreceptors have moderate affinity (AAV2quadY→F and AAV2quadY→F+T→V). AAV2MAXΔHS, the variant with ablated HS binding did not transduce cells in vitro, but was highly efficient at transducing photoreceptors when delivered subretinally.

Conclusion:

HS affinity of AAV2 based particles is a key factor in their ability to transduce photoreceptors from the vitreous. Photoreceptor transduction by AAV2 is not dependent on HS binding, suggesting another ligand-receptor pair is responsible for attachment of virus to the surface of photoreceptors. Therefore, changes in HS affinity are unlikely to negatively impact the recognition of the target cell type (photoreceptors), suggesting that further improvements in gene therapy of PR or RPE cells are achievable using the particles, vectors and methods described herein.

REFERENCES

The following references, to the extent that they provide exemplary procedural or other details supplementary to those set forth herein, are specifically incorporated herein by reference:

Acland, G M et al., "Gene therapy restores vision in a canine model of childhood blindness," *Nat. Genet.*, 28:92-95 (2001).

Akache, B et al., "The 37/67-kilodalton laminin receptor is a receptor for adeno-associated virus serotypes 8, 2, 3, and 9," *J. Virol.*, 80:9831-9836 (2006).

Ali, R R et al., "Gene transfer into the mouse retina mediated by an adeno-associated viral vector," *Hum. Mol. Genet.*, 5:591-594 (1996).

Allocca, M et al., "Novel adeno-associated virus serotypes efficiently transduce murine photoreceptors," *J. Virol.*, 81:11372-11380 (2007).

Al-Ubaidi, M R et al., "Proteomics profiling of the cone photoreceptor cell line, 661W," *Adv. Exp. Med. Biol.*, 613:301-311 (2008).

Aslanidi, G V et al., "Optimization of the capsid of recombinant 1 adeno-associated virus 2 (AAV2) vectors: The final threshold?" *PLoS One*, 8(3):e59142 (2013).

Aslanidi, G V et al., "High-efficiency transduction of human monocyte-derived dendritic cells by capsid-modified recombinant AAV2 vectors," *Vaccine*, 30:3908-3917 (2012).

Auricchio, A et al., "Exchange of surface proteins impacts on viral vector cellular specificity and transduction characteristics: the retina as a model," *Hum. Mol. Genet.*, 10:3075-3081 (2001).

Bainbridge, J W et al., "Effect of gene therapy on visual function in Leber's congenital amaurosis," *N. Engl. J. Med.*, 358:2231-2239 (2005).

Bartel, M A et al., "Directed evolution of novel adeno-associated viruses for therapeutic gene delivery," *Gene Ther.*, 19:694-700 (2012).

Beltran, W A et al., "rAAV2/5 gene-targeting to rods:dose-dependent efficiency and complications associated with different promoters," *Gene Ther.*, 17:1162-1174 (2010).

Bennett, J et al., "Stable transgene expression in rod photoreceptors after recombinant adeno-associated virus-mediated gene transfer to monkey retina," *Proc. Natl. Acad. Sci. USA*, 96:9920-9925 (1999).

Boye, S E et al., "The human rhodopsin kinase promoter in an AAV5 vector confers rod- and cone-specific expression in the primate retina," *Hum. Gene Ther.*, 23:1101-1115 (2012).

Boye, S E et al., "Functional and behavioral restoration of vision by gene therapy in the guanylate cyclase-1 (GC1) knockout mouse," *PLoS One*, 5:e11306 (2010).

Boye, S L et al., "Long-term preservation of cone photoreceptors and restoration of cone function by gene therapy in the guanylate cyclase-1 knockout (GC1KO) mouse," *Invest. Ophthalmol. Vis. Sci.*, 52:7098-7108 (2011).

Burger, C et al., "Recombinant AAV viral vectors pseudotyped with viral capsids from serotypes 1, 2, and 5 display differential efficiency and cell tropism after delivery to different regions of the central nervous system," *Mol. Ther.*, 10:302-317 (2004).

Chai, L and Morris, J E, "Distribution of heparan sulfate proteoglycans in embryonic chicken neural retina and isolated inner limiting membrane," *Curr. Eye Res.*, 13:669-677 (1994).

Chang B et al., "In-frame deletion in a novel centrosomal/ciliary protein CEP290/NPHP6 perturbs its interaction with RPGR and results in early-onset retinal degeneration in the rd16 mouse," *Hum. Mol. Genet.*, 15(11):1847-57 (2006).

Cho, E Y et al., "Expression pattern of glycoconjugates in rat retina as analysed by lectin histochemistry," *Histochem. J.*, 34:589-600 (2002).

Cideciyan, A V et al., "Human RPE65 gene therapy for Leber congenital amaurosis: persistence of early visual improvements and safety at 1 year," *Hum. Gene Ther.*, 20:999-1004 (2009).

Dalkara, D et al., "Inner limiting membrane barriers to AAV-mediated retinal transduction from the vitreous," *Mol. Ther.*, 17:2096-2102 (2009).

Daya, S and Berns, K I, "Gene therapy using adeno-associated virus vectors," *Clin. Microbiol. Rev.*, 21:583-593 (2008).

Gabriel, N et al., "Bio-engineering of AAV-2 capsid at specific serine, threonine or lysine residues improves its transduction efficiency in vitro and in vivo," *Hum. Gene Ther., Methods*, 24(2):80-93 (2013).

Gregg R G et al., "Identification of the gene and the mutation responsible for the mouse nob phenotype," *Invest. Ophthalmol. Vis. Sci.*, 44:378-384 (2003).

Haire, S E et al., "Light-driven cone arrestin translocation in cones of postnatal guanylate cyclase-1 knockout mouse retina treated with AAV-GC1," *Invest. Ophthalmol. Vis. Sci.*, 47:3745-3753 (2006).

Jacobson, S G et al., "Safety of recombinant adeno-associated virus type 2-RPE65 vector delivered by ocular sub-retinal injection," *Mol. Ther.*, 13:1074-1084 (2006).

Jacobson, S G et al., "Gene therapy for leber congenital amaurosis caused by RPE65 mutations: safety and efficacy in 15 children and adults followed up to 3 years," *Arch. Ophthalmol.*, 130:9-24 (2012).

Kaludov, N et al., "Adeno-associated virus serotype 4 (AAV4) and AAV5 both require sialic acid binding for hemagglutination and efficient transduction but differ in sialic acid linkage specificity," *J. Virol.*, 75:6884-6893 (2001).

Karali, M et al., "MicroRNA-restricted transgene expression in the retina," *PLoS One*, 6:e22166 (2011).

Karali, M et al., "miRNeye: a microRNA expression atlas of the mouse eye," *BMC Genomics*, 11:715 (2010).

Khani, S C et al., "AAV-mediated expression targeting of rod and cone photoreceptors with a human rhodopsin kinase promoter," *Invest. Ophthalmol. Vis. Sci.*, 48:3954-3961 (2007).

Klimczak, R R, "A novel adeno-associated viral variant for efficient and selective intravitreal transduction of rat Muller cells," *PLoS One*, 4:e7467 (2009).

Li, C et al., "Single amino acid modification of adeno-associated virus capsid changes transduction and humoral immune profiles," *J. Virol.*, 86:7752-7759 (2012).

Lotery, A J et al., "Adeno-associated virus type 5: transduction efficiency and cell-type specificity in the primate retina," *Hum. Gene Ther.*, 14:1663-1671 (2003).

Maguire, A M et al., "Safety and efficacy of gene transfer for Leber's congenital amaurosis," *N. Engl. J. Med.*, 358:2240-2248 (2008).

Matsumoto, B et al., "Topographic variations in the rabbit and primate internal limiting membrane," *Invest. Ophthalmol. Vis. Sci.*, 25:71-82 (1984).

Mussolino, C et al., "AAV-mediated photoreceptor transduction of the pig cone-enriched retina," *Gene Ther.*, 18:637-645 (2011).

Pang, J J et al., "Long-term retinal function and structure rescue using capsid mutant AAV8 vector in the rd10 mouse, a model of recessive retinitis pigmentosa," *Mol. Ther.*, 19:234-242 (2011).

Pang, J J et al., "AAV-mediated cone rescue in a naturally occurring mouse model of CNGA3-achromatopsia," *PLoS One*, 7:e35250 (2012).

Pardue M T et al., "A naturally occurring mouse model of X-linked congenital stationary night blindness," *Invest. Ophthalmol. Vis. Sci.*, 39:2443-2449 (1998).

Petersen-Jones, S M et al., "AAV retinal transduction in a large animal model species: comparison of a self-complementary AAV2/5 with a single-stranded AAV2/5 vector," *Mol. Vis.*, 15:1835-1842 (2009).

Petrs-Silva, H et al., "Novel properties of tyrosine-mutant AAV2 vectors in the mouse retina," *Mol. Ther.*, 19:293-301 (2011).

Petrs-Silva, H et al., "High-efficiency transduction of the mouse retina by tyrosine-mutant AAV serotype vectors," *Mol. Ther.*, 17:463-471 (2009).

Pulicherla, N and Asokan, A, "Peptide affinity reagents for AAV capsid recognition and purification," *Gene Ther.*, 18:1020-1024 (2011).

Rabinowitz, J E et al., "Cross-packaging of a single adeno-associated virus (AAV) type 2 vector genome into multiple AAV serotypes enables transduction with broad specificity," *J. Virol.*, 76:791-801 (2002).

Raupp, C et al., "The threefold protrusions of adeno-associated virus type 8 are involved in cell surface targeting as well as postattachment processing," *J. Virol.*, 86:9396-9408 (2012).

Ryals, R C et al., "Quantifying transduction efficiencies of unmodified and tyrosine capsid mutant AAV vectors in vitro using two ocular cell lines," *Mol. Vis.*, 17:1090-1102 (2011).

Stieger, K et al., "Subretinal delivery of recombinant AAV serotype 8 vector in dogs results in gene transfer to neurons in the brain," *Mol. Ther.*, 16:916-923 (2008).

Summerford, C and Samulski, R J, "Membrane-associated heparan sulfate proteoglycan is a receptor for adeno-associated virus type 2 virions," *J. Virol.*, 72:1438-1445 (1988).

Tan, E et al., "Expression of cone-photoreceptor-specific antigens in a cell line derived from retinal tumors in transgenic mice," *Invest. Ophthalmol. Vis. Sci.*, 45:764-768 (2004).

Vandenberghe, L H et al., "Cone and rod transduction with alternative AAV serotypes in the macula of non-human primates," Conference Proceedings, *Assoc. Res. Vis. Ophthalmol.*, (ARVO), Ft. Lauderdale, Fla. (2011).

Vandenberghe, L H et al., "Dosage thresholds for AAV2 and AAV8 photoreceptor gene therapy in monkey," *Sci. Transl. Med.*, 3:88ra54 (2011).

Weber, M et al., "Recombinant adeno-associated virus serotype 4 mediates unique and exclusive long-term transduction of retinal pigmented epithelium in rat, dog, and nonhuman primate after subretinal delivery," *Mol. Ther.*, 7:774-781 (2003).

Wensel, T G et al., "Rhodopsin-EGFP knock-ins for imaging quantal gene alterations," *Vision Res.*, 45:3445-3453 (2005).

Wright, A F et al., "Photoreceptor degeneration: genetic and mechanistic dissection of a complex trait," *Nat. Rev. Genet.*, 11:273-284 (2010).

Yang, G S et al., "Virus-mediated transduction of murine retina with adeno-associated virus: effects of viral capsid and genome size," *J. Virol.*, 76:7651-7660 (2002).

Yin, L et al., "Intravitreal injection of AAV2 transduces macaque inner retina," *Invest. Ophthalmol. Vis. Sci.*, 52:2775-2783 (2011).

Thong, L et al., "Next generation of adeno-associated virus 2 vectors: point mutations in tyrosines lead to high-efficiency transduction at lower doses," *Proc. Natl. Acad. Sci. USA*, 105:7827-7832 (2008).

Zolotukhin, S et al., "Production and purification of serotype 1, 2, and 5 recombinant adeno-associated viral vectors," Methods, 28:158-167 (2002).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A recombinant adeno-associated viral (rAAV) particle comprising:
a modified capsid protein, wherein the modified capsid protein comprises non-native amino acid substitutions at amino acid residues of a wild-type AAV2 capsid protein as set forth in SEQ ID NO:2, wherein the non-native amino acid substitutions comprise:
(a) Y444F, T491V, Y500F, R585S, R588T, R487G, and Y730F;
(b) Y444F, T491V, Y500F, R585S, and Y730F;
(c) Y444F, T491V, Y500F, R588T, and Y730F; or
(d) Y444F, T491V, Y500F, R585S, R588T, and Y730F,
or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

2. The rAAV particle of claim 1, wherein the transduction efficiency of the particle is about 2- to about 50-fold higher in the one or more photoreceptor or RPE cells than that of a particle that comprises a corresponding, unmodified, wild-type capsid protein.

3. The rAAV particle of claim 1, wherein the particle comprises a polynucleotide comprising a nucleic acid segment that encodes a diagnostic or therapeutic molecule operably linked to a promoter that is capable of expressing the nucleic acid segment in one or more photoreceptors or retinal pigment epithelial cells of a mammalian eye.

4. The rAAV particle of claim 3, wherein the nucleic acid segment expresses or encodes in one or more photoreceptor cells or RPE cells of a mammalian eye, a polypeptide, a peptide, a ribozyme, a peptide nucleic acid, an siRNA, an RNAi, an antisense oligonucleotide, an antisense polynucleotide, an antibody, an antigen binding fragment, or any combination thereof.

5. A nucleic acid vector that encodes a modified capsid protein, wherein the modified capsid protein comprises non-native amino acid substitutions at amino acid residues of a wild-type AAV2 capsid protein as set forth in SEQ ID NO:2, wherein the non-native amino acid substitutions comprise:
(a) Y444F, T491V, Y500F, R585S, R588T, R487G, and Y730F;
(b) Y444F, T491V, Y500F, R585S, and Y730F;
(c) Y444F, T491V, Y500F, R588T, and Y730F; or
(d) Y444F, T491V, Y500F, R585S, R588T, and Y730F,
or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

6. The nucleic acid vector of claim 5, wherein the transduction efficiency of a particle comprising the modified capsid protein is about 2- to about 50-fold higher in one or more photoreceptor or RPE cells than that of a particle that comprises a corresponding, unmodified, wild-type capsid protein.

7. The rAAV particle of claim 1, wherein the non-native amino acid substitutions further comprise an E530K substitution in the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

8. The nucleic acid vector of claim 5, wherein the non-native amino acid substitutions further comprise an E530K substitution in the wild-type AAV2 capsid protein as set forth in SEQ ID NO:2, or at equivalent amino acid positions corresponding thereto in any one of the wild-type AAV1, AAV3, AAV4, AAV5, AAV6, AAV7, AAV9, or AAV10 capsid proteins, as set forth, respectively, in SEQ ID NO:1, SEQ ID NO:3, SEQ ID NO:4, SEQ ID NO:5, SEQ ID NO:6, SEQ ID NO:7, SEQ ID NO:9, or SEQ ID NO:10.

* * * * *

SEQUENCE LISTING

```
<160> NUMBER OF SEQ ID NOS: 10

<210> SEQ ID NO 1
<211> LENGTH: 736
<212> TYPE: PRT
<213> ORGANISM: adeno-associated virus 1

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205
```

-continued

```
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
            245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
            275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
            325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
            355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
            405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
    435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
            485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
    515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
            565                 570                 575
Phe Gly Thr Val Ala Val Asn Phe Gln Ser Ser Ser Thr Asp Pro Ala
            580                 585                 590
Thr Gly Asp Val His Ala Met Gly Ala Leu Pro Gly Met Val Trp Gln
            595                 600                 605
Asp Arg Asp Val Tyr Leu Gln Gly Pro Ile Trp Ala Lys Ile Pro His
    610                 615                 620
```

```
Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 2
<211> LENGTH: 735
<212> TYPE: PRT
<213> ORGANISM: adeno-associated virus 2

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
            165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
            260                 265                 270
```

```
Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
        530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
                580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
        610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685
```

```
Glu Asn Ser Lys Arg Trp Asn Pro Glu Ile Gln Tyr Thr Ser Asn Tyr
    690             695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 3
<211> LENGTH: 736
<212> TYPE: PRT
<213> ORGANISM: Adeno-associated virus 3

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
                20                  25                  30

Lys Ala Asn Gln Gln His Gln Asp Asn Arg Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Gly
130                 135                 140

Ala Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Arg Gly Val Thr Gln Asn Asp Gly Thr Thr Thr Ile Ala Asn Asn Leu
                325                 330                 335
```

-continued

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Gly Thr Val Asn His Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 734
```

<212> TYPE: PRT
<213> ORGANISM: Adeno-associated virus 4

<400> SEQUENCE: 4

```
Met Thr Asp Gly Tyr Leu Pro Asp Trp Leu Glu Asp Asn Leu Ser Glu
1               5                   10                  15
Gly Val Arg Glu Trp Trp Ala Leu Gln Pro Gly Ala Pro Lys Pro Lys
                20                  25                  30
Ala Asn Gln Gln His Gln Asp Asn Ala Arg Gly Leu Val Leu Pro Gly
            35                  40                  45
Tyr Lys Tyr Leu Gly Pro Gly Asn Gly Leu Asp Lys Gly Glu Pro Val
        50                  55                  60
Asn Ala Ala Asp Ala Ala Ala Leu Glu His Asp Lys Ala Tyr Asp Gln
65                  70                  75                  80
Gln Leu Lys Ala Gly Asp Asn Pro Tyr Leu Lys Tyr Asn His Ala Asp
                85                  90                  95
Ala Glu Phe Gln Gln Arg Leu Gln Gly Asp Thr Ser Phe Gly Gly Asn
            100                 105                 110
Leu Gly Arg Ala Val Phe Gln Ala Lys Lys Arg Val Leu Glu Pro Leu
        115                 120                 125
Gly Leu Val Glu Gln Ala Gly Glu Thr Ala Pro Gly Lys Lys Arg Pro
130                 135                 140
Leu Ile Glu Ser Pro Gln Gln Pro Asp Ser Ser Thr Gly Ile Gly Lys
145                 150                 155                 160
Lys Gly Lys Gln Pro Ala Lys Lys Lys Leu Val Phe Glu Asp Glu Thr
                165                 170                 175
Gly Ala Gly Asp Gly Pro Pro Glu Gly Ser Thr Ser Gly Ala Met Ser
            180                 185                 190
Asp Asp Ser Glu Met Arg Ala Ala Ala Gly Gly Ala Val Glu Gly
        195                 200                 205
Gly Gln Gly Ala Asp Gly Val Gly Asn Ala Ser Gly Asp Trp His Cys
210                 215                 220
Asp Ser Thr Trp Ser Glu Gly His Val Thr Thr Thr Ser Thr Arg Thr
225                 230                 235                 240
Trp Val Leu Pro Thr Tyr Asn Asn His Leu Tyr Lys Arg Leu Gly Glu
                245                 250                 255
Ser Leu Gln Ser Asn Thr Tyr Asn Gly Phe Ser Thr Pro Trp Gly Tyr
            260                 265                 270
Phe Asp Phe Asn Arg Phe His Cys His Phe Ser Pro Arg Asp Trp Gln
        275                 280                 285
Arg Leu Ile Asn Asn Asn Trp Gly Met Arg Pro Lys Ala Met Arg Val
290                 295                 300
Lys Ile Phe Asn Ile Gln Val Lys Glu Val Thr Thr Ser Asn Gly Glu
305                 310                 315                 320
Thr Thr Val Ala Asn Asn Leu Thr Ser Thr Val Gln Ile Phe Ala Asp
                325                 330                 335
Ser Ser Tyr Glu Leu Pro Tyr Val Met Asp Ala Gly Gln Glu Gly Ser
            340                 345                 350
Leu Pro Pro Phe Pro Asn Asp Val Phe Met Val Pro Gln Tyr Gly Tyr
        355                 360                 365
Cys Gly Leu Val Thr Gly Asn Thr Ser Gln Gln Thr Asp Arg Asn
        370                 375                 380
Ala Phe Tyr Cys Leu Glu Tyr Phe Pro Ser Gln Met Leu Arg Thr Gly
385                 390                 395                 400
```

-continued

Asn Asn Phe Glu Ile Thr Tyr Ser Phe Glu Lys Val Pro Phe His Ser
            405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
        450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
        530                 535                 540

Gln Asn Gly Asn Thr Ala Thr Val Pro Gly Thr Leu Ile Phe Thr Ser
545                 550                 555                 560

Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
        610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
        690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 5
<211> LENGTH: 724
<212> TYPE: PRT
<213> ORGANISM: Adeno-associated virus 5

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly

```
            35                  40                  45
Tyr Asn Tyr Leu Gly Pro Gly Asn Gly Leu Asp Arg Gly Glu Pro Val
 50                  55                  60
Asn Arg Ala Asp Glu Val Ala Arg Glu His Asp Ile Ser Tyr Asn Glu
 65                  70                  75                  80
Gln Leu Glu Ala Gly Asp Asn Pro Tyr Leu Lys Tyr Asn His Ala Asp
                 85                  90                  95
Ala Glu Phe Gln Glu Lys Leu Ala Asp Asp Thr Ser Phe Gly Gly Asn
            100                 105                 110
Leu Gly Lys Ala Val Phe Gln Ala Lys Arg Val Leu Glu Pro Phe
            115                 120                 125
Gly Leu Val Glu Glu Gly Ala Lys Thr Ala Pro Thr Gly Lys Arg Ile
            130                 135                 140
Asp Asp His Phe Pro Lys Arg Lys Lys Ala Arg Thr Glu Glu Asp Ser
145                 150                 155                 160
Lys Pro Ser Thr Ser Ser Asp Ala Glu Ala Gly Pro Ser Gly Ser Gln
                165                 170                 175
Gln Leu Gln Ile Pro Ala Gln Pro Ala Ser Ser Leu Gly Ala Asp Thr
            180                 185                 190
Met Ser Ala Gly Gly Gly Pro Leu Gly Asp Asn Asn Gln Gly Ala
            195                 200                 205
Asp Gly Val Gly Asn Ala Ser Gly Asp Trp His Cys Asp Ser Thr Trp
210                 215                 220
Met Gly Asp Arg Val Val Thr Lys Ser Thr Arg Thr Trp Val Leu Pro
225                 230                 235                 240
Ser Tyr Asn Asn His Gln Tyr Arg Glu Ile Lys Ser Gly Ser Val Asp
                245                 250                 255
Gly Ser Asn Ala Asn Ala Tyr Phe Gly Tyr Ser Thr Pro Trp Gly Tyr
            260                 265                 270
Phe Asp Phe Asn Arg Phe His Ser His Trp Ser Pro Arg Asp Trp Gln
            275                 280                 285
Arg Leu Ile Asn Asn Tyr Trp Gly Phe Arg Pro Arg Ser Leu Arg Val
            290                 295                 300
Lys Ile Phe Asn Ile Gln Val Lys Glu Val Thr Val Gln Asp Ser Thr
305                 310                 315                 320
Thr Thr Ile Ala Asn Asn Leu Thr Ser Thr Val Gln Val Phe Thr Asp
                325                 330                 335
Asp Asp Tyr Gln Leu Pro Tyr Val Val Gly Asn Gly Thr Glu Gly Cys
                340                 345                 350
Leu Pro Ala Phe Pro Pro Gln Val Phe Thr Leu Pro Gln Tyr Gly Tyr
            355                 360                 365
Ala Thr Leu Asn Arg Asp Asn Thr Glu Asn Pro Thr Glu Arg Ser Ser
            370                 375                 380
Phe Phe Cys Leu Glu Tyr Phe Pro Ser Lys Met Leu Arg Thr Gly Asn
385                 390                 395                 400
Asn Phe Glu Phe Thr Tyr Asn Phe Glu Glu Val Pro Phe His Ser Ser
                405                 410                 415
Phe Ala Pro Ser Gln Asn Leu Phe Lys Leu Ala Asn Pro Leu Val Asp
                420                 425                 430
Gln Tyr Leu Tyr Arg Phe Val Ser Thr Asn Thr Gly Gly Val Gln
            435                 440                 445
Phe Asn Lys Asn Leu Ala Gly Arg Tyr Ala Asn Thr Tyr Lys Asn Trp
450                 455                 460
```

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: Adeno-associated virus 6

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

```
Asn Leu Gly Arg Ala Val Phe Gln Ala Lys Lys Arg Val Leu Glu Pro
        115                 120                 125

Phe Gly Leu Val Glu Glu Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
                180                 185                 190

Ala Thr Pro Ala Ala Val Gly Pro Thr Thr Met Ala Ser Gly Gly Gly
            195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525
```

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
            565                 570                 575

Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
    595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 7
<211> LENGTH: 737
<212> TYPE: PRT
<213> ORGANISM: Adeno-associated virus 7

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

```
Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
            195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
            450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
            530                 535                 540

Phe Gly Lys Thr Gly Ala Thr Asn Lys Thr Thr Leu Glu Asn Val Leu
545                 550                 555                 560

Met Thr Asn Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590
```

```
Gln Thr Gln Val Val Asn Asn Gln Gly Ala Leu Pro Gly Met Val Trp
            595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 8
<211> LENGTH: 738
<212> TYPE: PRT
<213> ORGANISM: Adeno-associated virus 8
<220> FEATURE:
<221> NAME/KEY: misc_feature
<222> LOCATION: (566)..(566)
<223> OTHER INFORMATION: Xaa can be any naturally occurring amino acid

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205
```

```
Gly Ala Pro Met Ala Asp Asn Glu Gly Ala Asp Gly Val Gly Ser
    210             215             220

Ser Ser Gly Asn Trp His Cys Asp Ser Thr Trp Leu Gly Asp Arg Val
225             230             235             240

Ile Thr Thr Ser Thr Arg Thr Trp Ala Leu Pro Thr Tyr Asn Asn His
                245             250             255

Leu Tyr Lys Gln Ile Ser Asn Gly Thr Ser Gly Ala Thr Asn Asp
            260             265             270

Asn Thr Tyr Phe Gly Tyr Ser Thr Pro Trp Gly Tyr Phe Asp Phe Asn
        275             280             285

Arg Phe His Cys His Phe Ser Pro Arg Asp Trp Gln Arg Leu Ile Asn
    290             295             300

Asn Asn Trp Gly Phe Arg Pro Lys Arg Leu Ser Phe Lys Leu Phe Asn
305             310             315             320

Ile Gln Val Lys Glu Val Thr Gln Asn Glu Gly Thr Lys Thr Ile Ala
                325             330             335

Asn Asn Leu Thr Ser Thr Ile Gln Val Phe Thr Asp Ser Glu Tyr Gln
            340             345             350

Leu Pro Tyr Val Leu Gly Ser Ala His Gln Gly Cys Leu Pro Pro Phe
        355             360             365

Pro Ala Asp Val Phe Met Ile Pro Gln Tyr Gly Tyr Leu Thr Leu Asn
370             375             380

Asn Gly Ser Gln Ala Val Gly Arg Ser Ser Phe Tyr Cys Leu Glu Tyr
385             390             395             400

Phe Pro Ser Gln Met Leu Arg Thr Gly Asn Asn Phe Gln Phe Thr Tyr
                405             410             415

Thr Phe Glu Asp Val Pro Phe His Ser Ser Tyr Ala His Ser Gln Ser
            420             425             430

Leu Asp Arg Leu Met Asn Pro Leu Ile Asp Gln Tyr Leu Tyr Tyr Leu
        435             440             445

Ser Arg Thr Gln Thr Thr Gly Gly Thr Ala Asn Thr Gln Thr Leu Gly
450             455             460

Phe Ser Gln Gly Gly Pro Asn Thr Met Ala Asn Gln Ala Lys Asn Trp
465             470             475             480

Leu Pro Gly Pro Cys Tyr Arg Gln Gln Arg Val Ser Thr Thr Thr Gly
                485             490             495

Gln Asn Asn Asn Ser Asn Phe Ala Trp Thr Ala Gly Thr Lys Tyr His
            500             505             510

Leu Asn Gly Arg Asn Ser Leu Ala Asn Pro Gly Ile Ala Met Ala Thr
        515             520             525

His Lys Asp Asp Glu Glu Arg Phe Phe Pro Ser Asn Gly Ile Leu Ile
530             535             540

Phe Gly Lys Gln Asn Ala Ala Arg Asp Asn Ala Asp Tyr Ser Asp Val
545             550             555             560

Met Leu Thr Ser Glu Xaa Glu Ile Lys Thr Thr Asn Pro Val Ala Thr
                565             570             575

Glu Glu Tyr Gly Ile Val Ala Asp Asn Leu Gln Gln Gln Asn Thr Ala
            580             585             590

Pro Gln Ile Gly Thr Val Asn Ser Gln Gly Ala Leu Pro Gly Met Val
        595             600             605

Trp Gln Asn Arg Asp Val Tyr Leu Gln Gly Pro Ile Trp Ala Lys Ile
610             615             620
```

-continued

```
Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
            645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 9
<211> LENGTH: 736
<212> TYPE: PRT
<213> ORGANISM: Adeno-associated virus 9

<400> SEQUENCE: 9

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
```

```
            675                 680                 685
Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 10
<211> LENGTH: 738
<212> TYPE: PRT
<213> ORGANISM: Adeno-associated virus 10

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320
```

-continued

```
Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720
```

```
Gly Thr Tyr Ser Glu Pro Arg Pro Ile Gly Thr Arg Tyr Leu Thr Arg
            725                 730                 735
Asn Leu
```